(12) United States Patent
DeFilippi et al.

(10) Patent No.: US 6,395,522 B1
(45) Date of Patent: *May 28, 2002

(54) BIOLOGICALLY ACTIVE SUPPORT CONTAINING BOUND ADSORBENT PARTICLES AND MICROORGANISMS FOR WASTE STREAM PURIFICATION

(75) Inventors: Louis J. DeFilippi, Mount Prospect; Francis S. Lupton, Evanston, both of IL (US)

(73) Assignee: AlliedSignal Inc., Morristown, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/178,343

(22) Filed: Jan. 6, 1994

Related U.S. Application Data

(63) Continuation of application No. 07/763,735, filed on Sep. 23, 1991, now abandoned, which is a continuation-in-part of application No. 07/430,709, filed on Nov. 2, 1989, now abandoned.

(51) Int. Cl.⁷ .................. C12N 11/08; C12M 1/00; C02F 3/00
(52) U.S. Cl. ............ 435/180; 210/601; 210/616; 210/617; 210/620; 435/176; 435/177; 435/262.5; 435/289.1
(58) Field of Search ............... 435/176, 177, 435/178, 180, 181, 262.5, 289.1; 210/601, 616, 617, 620

(56) References Cited

U.S. PATENT DOCUMENTS

| 4,045,609 A | | 8/1977 | Hart ........................ 428/253 |
| 4,046,939 A | | 9/1977 | Hart ........................ 428/311 |
| 4,566,971 A | * | 1/1986 | Reimann et al. ............ 210/616 |
| 4,983,299 A | * | 1/1991 | Lupton et al. ............. 210/609 |
| 5,057,221 A | * | 10/1991 | Bryant et al. .............. 210/617 |
| 5,217,616 A | * | 6/1993 | Sanyal et al. .............. 210/617 |

FOREIGN PATENT DOCUMENTS

| WO | 9011970 | * 10/1990 |

* cited by examiner

*Primary Examiner*—David M. Naff
(74) *Attorney, Agent, or Firm*—Colleen D. Szuch

(57) ABSTRACT

A biologically active support is provided for removal of pollutants such as aliphatics, aromatics, heteroaromatics and halogenated derivatives from waste streams. The support contains a particulate adsorbent such as activated carbon bound by a polymer binder to a substrate such as a polymeric foam, and a bound pollutant-degrading microorganism. The adsorbent adsorbs a target pollutant, and the microorganism degrades the pollutant. Preferably, the microorganism is aerobic and the binder has a $T_g$ of lower than or equal to about 25° C. The adsorbent adsorbs excess pollutant when the pollutant concentration increases and releases the pollutant when the concentration decreases. This maintains the pollutant concentration at a level which does not inhibit the microorganism. The biologically active support can be used in conventional biological waste treatment systems such as continuous stirred reactors, fixed-bed reactors and fluidized bed reactors.

26 Claims, 9 Drawing Sheets

A = SUBSTRATE
B = ADSORBANT

A = SUBSTRATE
B = ADSORBANT
C = BINDER

A = SUBSTRATE
B = ADSORBANT
C = BINDER

BIOLOGICALLY ACTIVE SUPPORT CONTAINING BOUND ADSORBENT PARTICLES AND MICROORGANISMS FOR WASTE STREAM PURIFICATION

RELATED APPLICATION

This application is a continuation of application Ser. No. 07/763,735, filed Sep. 23, 1991, now abandoned, which is a continuation-in-part of application Ser. No. 07/430,709, filed Nov. 2, 1989, now abandoned, which is related to application Ser. No. 07/335,610, filed Apr. 10, 1989, now U.S. Pat. No. 4,983,299.

BACKGROUND OF THE INVENTION

1. Field of the Invention

This invention relates generally to an adsorbent coated biologically active biomass support for use in biological processes for the purification of waste streams, as for example industrial and municipal waste waters and to products, apparatuses and processes for use of such media. More particularly, the present invention relates to such support media which comprises a rigid or semi-rigid substrate that has an adsorbent material, capable of adsorbing pollutants and promoting their subsequent biodegradation by attached and immobilized microorganisms, bonded to the substrate, and to a bioreactor comprising the aforesaid biologically active biomass.

2. Prior Art

One of the hallmarks of contemporary civilization is that each increment of technological progress almost invariably is accompanied by a similar increment of environmental regress. As the pace of technological advances quickens, so does the march of environmental deterioration. The realization of environmental damage has occurred only relatively recently, so that present society sometimes finds itself burdened with the accumulated sins of the not-too-distant past. But another hallmark of current society is its acceptance of the undesirability of environmental degradation coupled with a determination to minimize and even reverse it wherever possible. Although the return of ground waters to their pristine condition of an earlier era is not a realistic goal, there is a genuine determination to make our waters as pure as possible. Environmental agencies have set limits for many common industrial pollutants, and as methods of pollution reduction have become more successful in reducing or removing pollutants from waste water, environmental regulations have become more stringent, resulting in an ever tightening spiral whose goal is to reduce pollutants in waste water to that minimum which is technologically feasible.

Among the methods employed to reduce or remove pollutants, bioremediation constitutes an effective and highly desirable approach. Quite broadly in bioremediation pollutants serve as a food source, generally as a source of carbon and/or nitrogen, for microorganisms. Bacterial metabolism converts the pollutants to metabolites generally with a simple chemical structure, sometimes degrading the pollutants completely to carbon dioxide and water in an aerobic process, or to methane in an anaerobic process. But in any event, the metabolites usually have no adverse environmental effects.

Various bioremediation processes are known. For example, U.S. Pat. No. 4,634,672 describes biologically active compositions for purifying waste water and air which comprises a polyurethane hydrogel containing (i) surface active coal having a specific surface according to BET of above 50 $m^2/g$, a polymer having cationic groups and cells which have enzymatic activity and are capable of growth. U.S. Pat. No. 4,681,852 describes a process for biological purification of waste water and/or air by contacting the water or air with the biologically active composition of U.S. Pat. No. 4,634,672. The experimental examples of these patents indicate that the process is not effective for reducing contaminant concentrations in the effluent strain to less than 44 parts per million (ppm). This is not acceptable since the Environmental Protection Agency (EPA) in some instances has mandated that concentration for some contaminants (such as phenol) in effluent waste streams must be as low as 20 parts-per-billion (ppb). (See Environmental Protection Agency 40 CFR Parts 414 and 416. Organic Chemicals and Plastics and Synthetic Fibers Category Effluent Limitations, Guidelines Retreatment Standards, and new Source Performance Standards, Federal Register, Volume 52, No. 214, Thursday, Nov. 5. 1987 Public and Regulations 42522.)

Both U.S. Pat. Nos. 3,904,518 and 4,069,148 describe the addition of activated carbon or Fuller's earth to a suspension of biologically active solids (activated sludge) in waste water as an aid in phenol removal. The adsorbent presumably acts by preventing pollutants toxic to the bacteria from interfering with bacterial metabolic activity. The patentees' approach has matured into the so-called PACT process which has gained commercial acceptance despite its requisites of a long residence time, copious sludge formation with attendant sludge disposal problems, and the need to regenerate and replace spent carbon.

Rehm and coworkers have further refined the use of activated carbon in the aerobic oxidation of phenolic materials by using microorganisms immobilized on granular carbon as a porous biomass support system. Utilizing the propensity of microorganisms to grow on and remain attached to a surface, Rehm used a granular activated carbon support of high surface area (1300 $m^2/g$) to which cells were attached within the macropores of the support and on its surface, as a porous biomass support system in a loop reactor for phenol removal. H. M. Ehrhardt and H. J. Rehm, Appl. Microbiol. Biotechnol., 21, 32–6 (1985). The resulting "immobilized" cells exhibited phenol tolerance up to a level in the feed of about 15 g/L, whereas free cells showed a tolerance not more than 1.5 g/L. It was postulated that the activated carbon operated like a "buffer and depot" in protecting the immobilized microorganisms by adsorbing toxic phenol concentrations and setting low quantities of the adsorbed phenol free for gradual biodegradation. This work was somewhat refined using a mixed culture immobilized on activated carbon [A. Morsen and H. J. Rehm, Appl. Microbiol. Biotechnol., 26, 283–8 (1987)] where the investigators noted that a considerable amount of microorganisms had "grown out" into the aqueous medium, i.e., there was substantial sludge formation in their system.

Suidan and coworkers have done considerable research on the analogous anaerobic degradation of phenol using a packed bed of microorganisms attached to granular carbon [Y. T. Wang, M. T. Suidan and B. E. Rittman, Journal Water Pollut. Control Fed., 58 227–33 (1986)]. For example, using granular activated carbon of 16×20 mesh as a support medium for microorganisms in an expanded bed configuration, and with feed containing from 358–1432 mg phenol/L, effluent phenol levels of about 0.06 mg/L (60 ppb) were obtained at a hydraulic residence time (HRT) of about 24 hours. Somewhat later, a beri-saddle-packed bed and expanded bed granular activated carbon anaerobic reactor in series were used to show a high conversion of COD to methane, virtually all of which occurred in the expanded bed reactor; P. Fox, M. T. Suidan, and J. T. Pfeffer, ibid., 60, 86–92 (1988). The refractory nature of ortho- and meta-cresols toward degradation also was noted.

The impregnation of flexible polymeric foams with activated carbon is known to increase the ability of fabrics and garments to resist the passage of noxious chemicals and gases see for example, U.S. Pat. Nos. 4,045,609 and 4,046,939. However, these patents do not teach the use of these foams in waste water treatment, or that these foams are a superior immobilization support for the growth and activity of microorganisms.

Givens and Sack, 42nd Purdue University Industrial Waste Conference Proceedings, pp. 93–102 (1987), performed an extensive evaluation of a carbon impregnated polyurethane foam as a microbial support system for the aerobic removal of pollutants, including phenol. Porous polyurethane foam internally impregnated with activated carbon and having microorganisms attached externally was used in an activated sludge reactor, analogous to the Captor and Linpor processes which differ only in the absence of foam-entrapped carbon. The process was attended by substantial sludge formation and without any beneficial effect of carbon.

The Captor process itself utilizes porous polyurethane foam pads to provide a large external surface for microbial growth in an aeration tank for biological waste water treatment. The work described above is the Captor process modified by the presence of carbon entrapped within the foam. A two-year pilot plant evaluation of the Captor process itself showed substantial sludge formation with significantly lower microbial density than had been claimed. J. A. Heidman, R. C. Brenner and H. J. Shah, J. of Environmental Engineering, 114, 1077–96 (1988). A point to be noted, as will be revisited below, is that the Captor process is essentially an aerated sludge reactor where the pads are retained in an aeration tank by screens in the effluent line. Excess sludge needs to be continually removed by removing a portion of the pads via a conveyor and passing the pads through pressure rollers to squeeze out the solids.

H. Bettmann and H. J. Rehm, Appl. Microbial. Biotechnol., 22, 389–393 (1985) have employed a fluidized bed bioreactor for the successful continuous aerobic degradation of phenol at a hydraulic residence time of about 15 hours using *Pseudomonas putida* entrapped in a polyacrylamide-hydrazide gel. The use of microorganisms entrapped within polyurethane foams in aerobic oxidation of phenol in shake flasks also has been reported; A. M. Anselmo et al., Biotechnology B.L., 7, 889–894 (1985). The latter appears to be the sole report of micro-organisms entrapped within a foam used for biodegration of organic pollutants.

Known bioremediation processes suffer from a number of inherent advantages. For example, a major result of increased use of such processes is an ever increasing quantity of sludge, which presents a serious disposal problem because of increasingly restrictive policies on dumping or spreading untreated sludge on land and at sea. G. Michael Alsop and Richard A. Conroy, "Improved Thermal Sludge Conditioning by Treatment With Acids and Bases", *Journal WPCF*, Vol. 54, No. 2 (1982), T. Calcutt and R.

Frost, "Sludge Processing—Chances for Tomorrow", *Journal of the Institute of Water Pollution Control*, Vol. 86, No. 2 (1987) and "The Municipal Waste Landfill Crisis and A Response of New Technology", Prepared by United States Building Corporation, P.O. Box 49704, Los Angles, Calif. 90049 (Nov. 22, 1988). The cost of sludge disposal today may be several fold greater than the sum of other operating costs of waste water treatment.

Use of anaerobic sewage treatment systems has been offered as a solution to the sludge problem. William J. Jewel "Anaerobic Sewage Treatment", *Environ. Sci. Technol.*, Vol. 21, No. 1 (1987). The largest difference between aerobic and anaerobic systems is in cellular yield. More than half of the substrate removal by aerobic systems can yield new microbial mass or sludge, the yield under anaerobic conditions is usually less that 15% of the organic substances removed. However, anaerobic systems are limited in the number of substrate that they can degrade or metabolize, and are not able to degrade or metabolize polynuclear aromatic hydrocarbons and non-substituted aromatic hydrocarbons such as benzene, anthracene and phenanthrene which are often present along with phenol in industrial waste waters such as coal tar processing waste waters and coke processing waste waters (See Battersby, N. S. and Wilson, Valerie, "Survey of the Anaerobic Biodegradation Potential of Organic Chemicals in digesting Sludge", *Applied and Environmental Microbiology*, Vol. 55, No. 2, pp. 433–439 (February, 1989). And J. M. Thomas, M. D. Lee, M. J. Scott and C. H. Ward "Microbial Ecology of the Subsurface at an Abandoned Cresote Waste Site", Journal of Industrial Microbiology Volume 4, pp 109–120 (1989).

Another disadvantage inherent in some known bioremediation processes is that these processes do not reduce the levels of organic pollutants to reasonable levels preferable less than about 0.1 parts per million (ppm) at reasonable residence times (preferably less than about 24 hours). For example, in the process of U.S. Pat. Nos. 4,681,851 and 4,634,672 (See the specific examples), the concentration of phenol contaminants was not reduced below about 44 ppm. Thus, these processes are generally not effective for reduction of phenol to levels mandated by the EPA. (See Federal Register, Vol. 52, No. 214, pp. 42572 Nov. 5, 1987.)

SUMMARY OF THE INVENTION

This invention relates to a novel process for the purification of a wastestream, bioreactors for carrying out the purification process and novel support media for use therein.

The invention is directed to a process for purification of a wastestream comprising a pollutant which comprises: passing an aqueous influent stream, having a pollutant present at a first concentration(cl), through a bioreactor in the presence of a gas comprising an effective amount of oxygen, said bioreactor comprising a biologically active biomass which comprises a plurality of biologically active support materials, each of said support materials comprising substrate having an effective amount of an effective adsorbent for said pollutant on said substrate and having an effective amount of aerobic microorganisms capable of metabolizing said pollutant on said substrate, said adsorbent or a combination thereof, to provide an effluent stream in which the concentration said pollutant is less than cl;

wherein when the concentration of said pollutant in said influent stream is increased from $c_1$ to a second concentration ($c_2$) for a period of 1 hydraulic residence time (HRT), causing an increase in the concentration of pollutant in the effluent stream, the concentration of said pollutant in the effluent stream is less than or equal to about 0.15 $C_2$ within about ¹⁄₂₄ HRT or less after the end of said 1 HRT; and wherein upon decreasing the concentration of said pollutant in said influent to $C_1$ and maintaining the concentration of pollutant at cl for at least 1 HRT, the concentration of the pollutant in the effluent stream decreases to less than or equal to about 0.12 $C_1$ within about 1 HRT or less.

Several advantages flow from the novel process of this invention. An important benefit which flows from this invention is that our process is resistant to upset.

Resistant to upset describes the ability of the process to reduce efficiently the contaminant level of waste streams having a relatively high level of contaminants to a desired level, preventing intermittent contaminant levels in the effluent above a desired level. For example, in certain preferred embodiments of this invention, concentration levels of organic pollutants in the feed stream can be as high as about 5000 parts-per million (ppm) which through use of the process of this invention can be reduced to levels as low as 1 ppm, or 0.1 ppm or for that matter 20 parts-per-billion (ppb). This advantage is of immediate and substantial economic benefit in that it obviates the need for time consuming and expensive pretreatment processes for reducing the amount of contaminant in the aqueous stream directly exiting the manufacturing process before introducing the stream into a bioremediation process. Our process provides for continuous treatment of a waste stream such that the concentration of pollutant in the effluent stream is maintained below EPA mandated levels. In addition, since our process can remediate relatively high levels of pollutants, the likelihood of a pollutant-cotaining waste stream deactivating the microorganisms killing or hindering their pollutant-degrading ability is significantly reduced.

Another advantage of preferred embodiments of this invention is that the process can be used in a fixed bed reactor system to reduce relatively high levels of organic pollutants in aqueous feed streams to relatively low levels with the additional benefit of significantly less sludge formation than that from currently available systems, affording important advantages in sludge disposal costs.

Another unique advantage of this invention is that significant reductions in levels of organic contaminants contained in the effluent stream are obtained with reasonable hydraulic residence times as compared to prior art processes as for example, the process described in U.S. Pat. Nos. 4,634,672 and 4,681,851. For example, experimentation has demonstrated that in certain most preferred embodiments of the invention, the level of effluent phenol in phenol containing aqueous waste streams can be reduced to concentrations as low as 20 parts per billion at hydraulic residence times as short at 24 hours. This is also not a trivial benefit especially in view of the low levels of various organic pollutants such as phenol in aqueous waste streams from industrial processes set by the Environmental Protection Agency and the economic requirement that these reduced levels be obtained over reasonable time periods.

A As measured by its performance characteristic relative to prior art processes, the process of this invention is a marked improvement over the prior art and relative to the prior art represents a difference in kind rather than a difference in degree.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF THE PREFERRED EMBODIMENTS OF THE INVENTION

Figure 1:
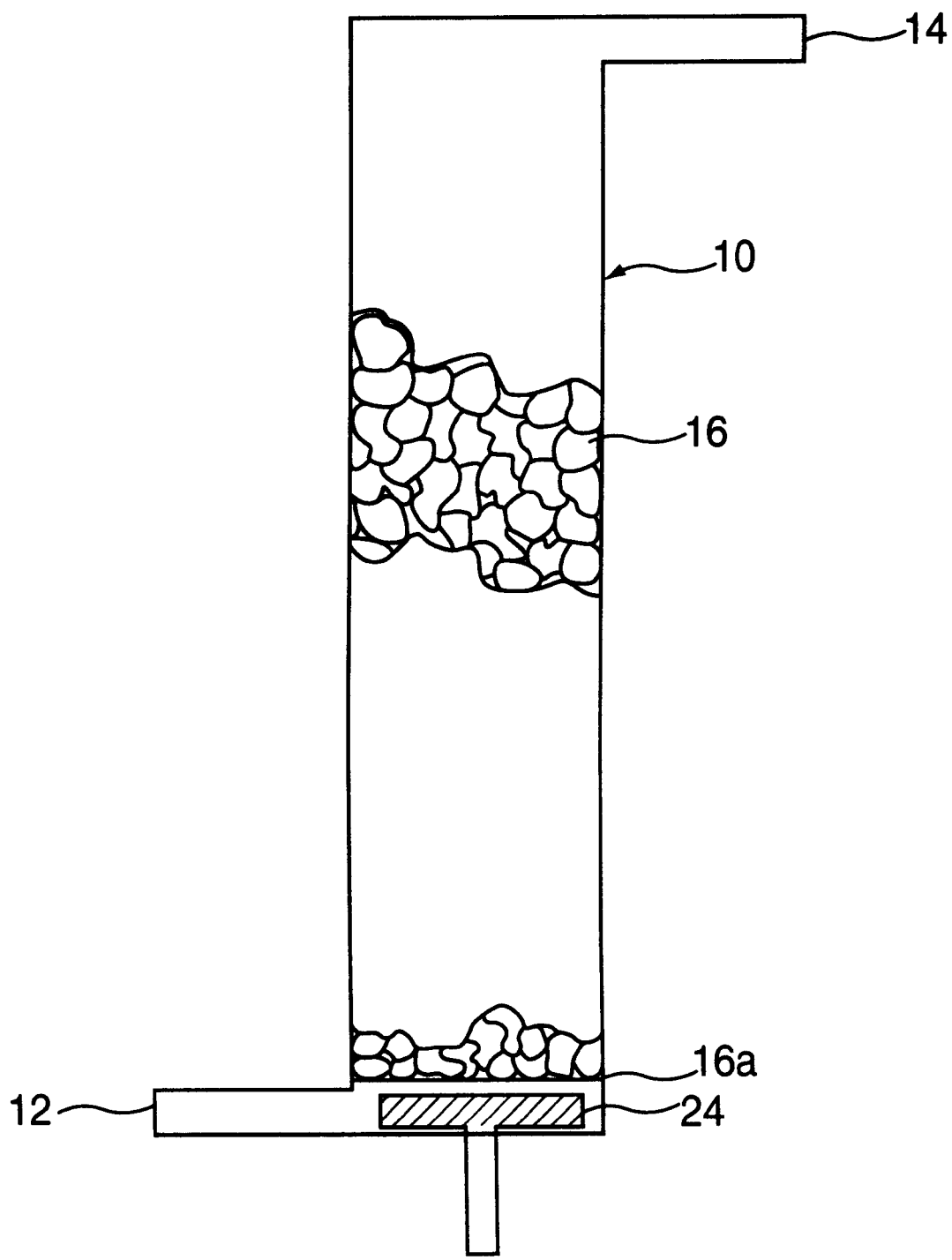
FIG. 1 is a cross-sectional side view of a vertical reactor for use in a preferred embodiments of the invention.
Figure 2:
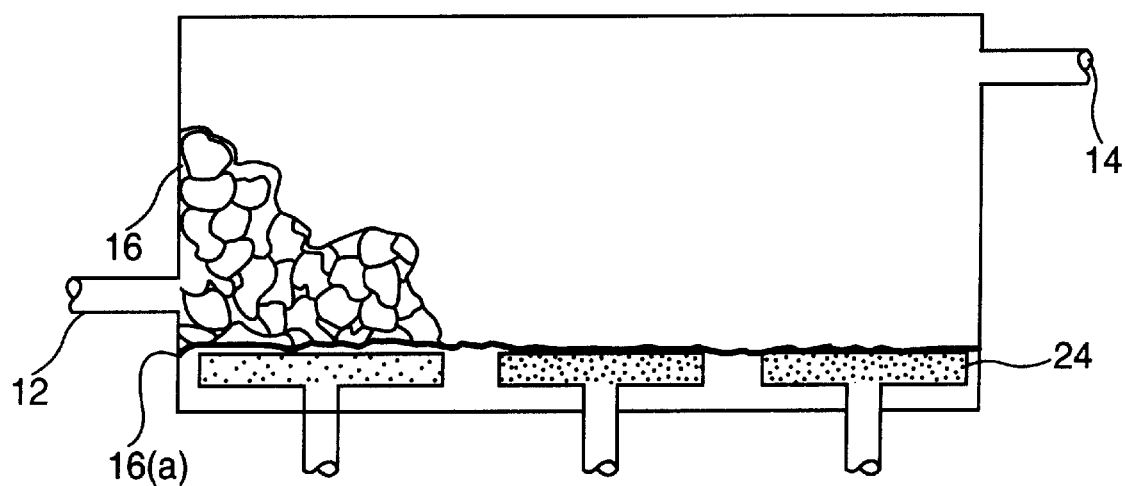
FIG. 2 is a cross-sectional side view of a horizontal reactor for use in the process of this invention.
Figure 3:
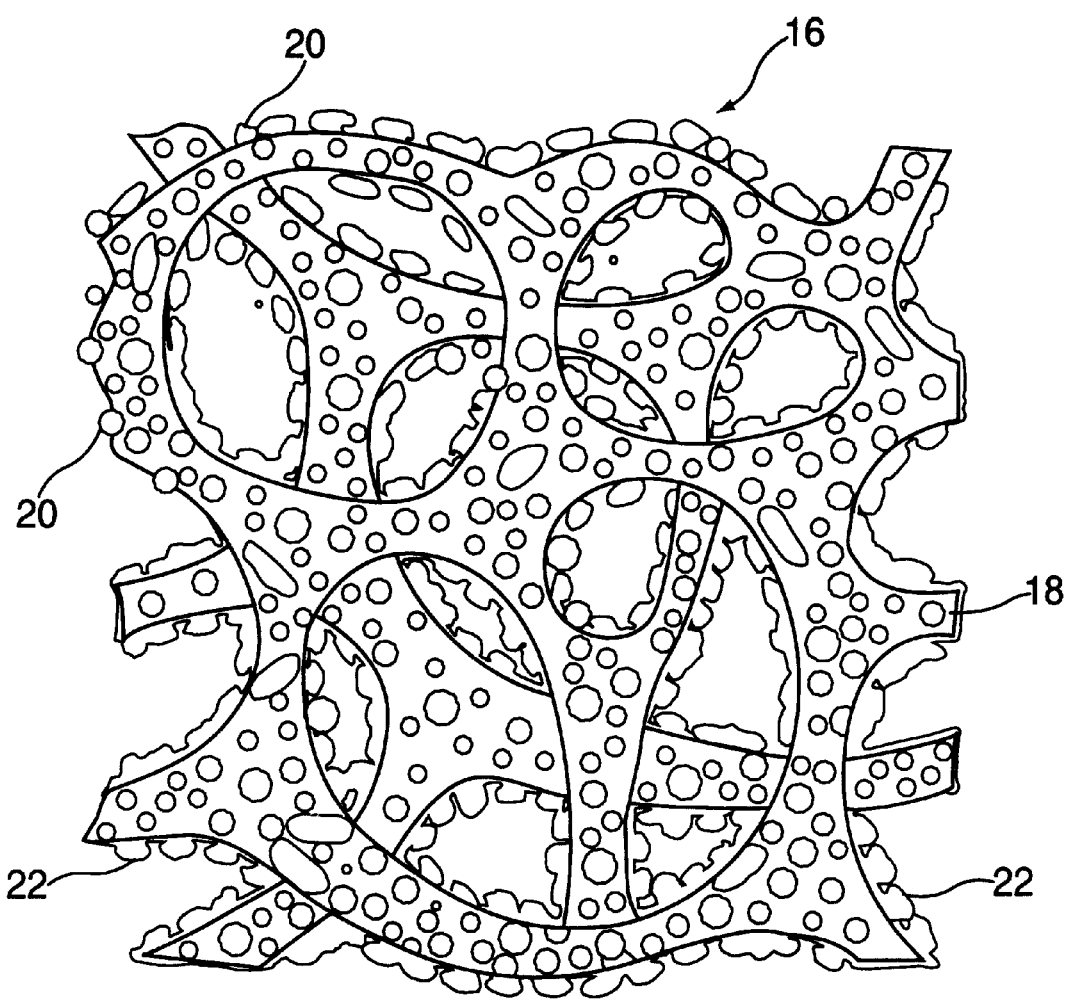
FIG. 3 is a cross-sectional view of a preferred biologically active particle for use in the process of this invention.
Figure 4:
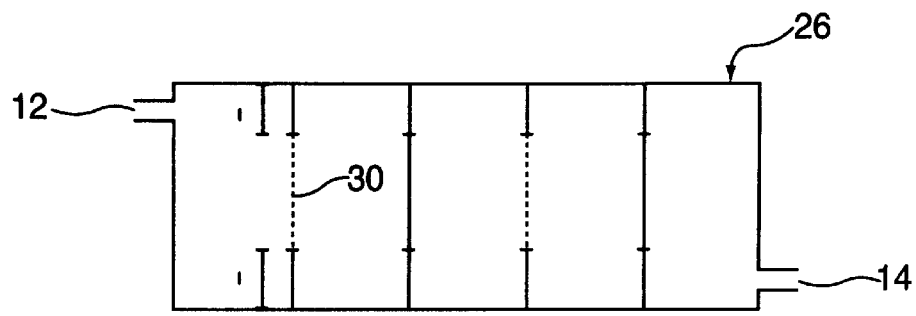
FIG. 4 is a cross-sectional top view of a reactor for use in the process of this invention having a cascading design.
Figure 5:
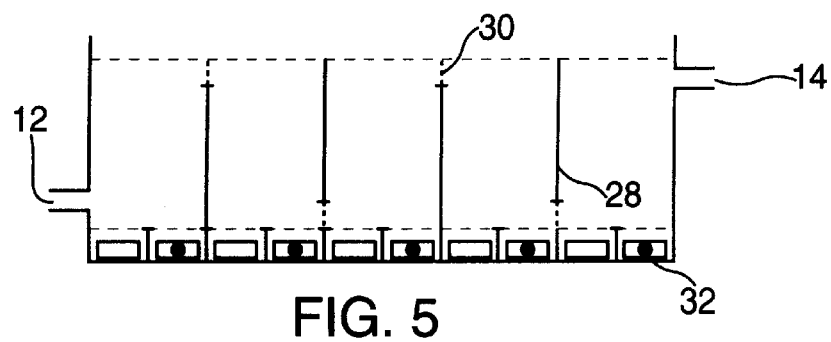
FIG. 5 is a side cross-sectional view of the reactor of FIG. 4.
Figure 6:
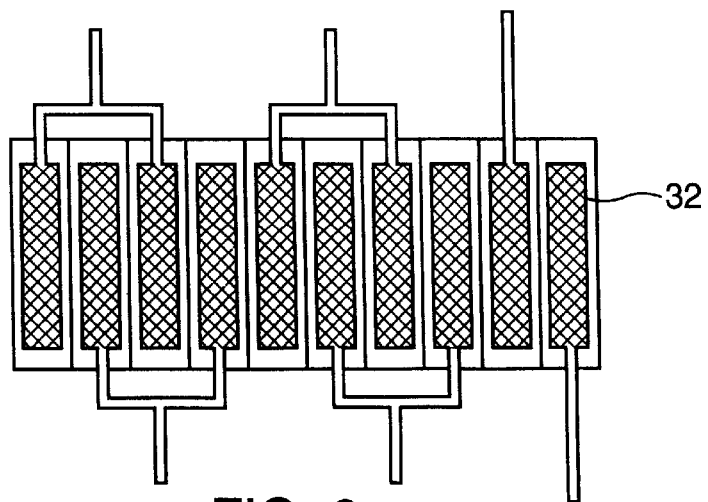
FIG. 6 is a top view of the reactor of FIG. 4 depicting the oxygenation system of the reactor of FIG. 4.
Figure 7:
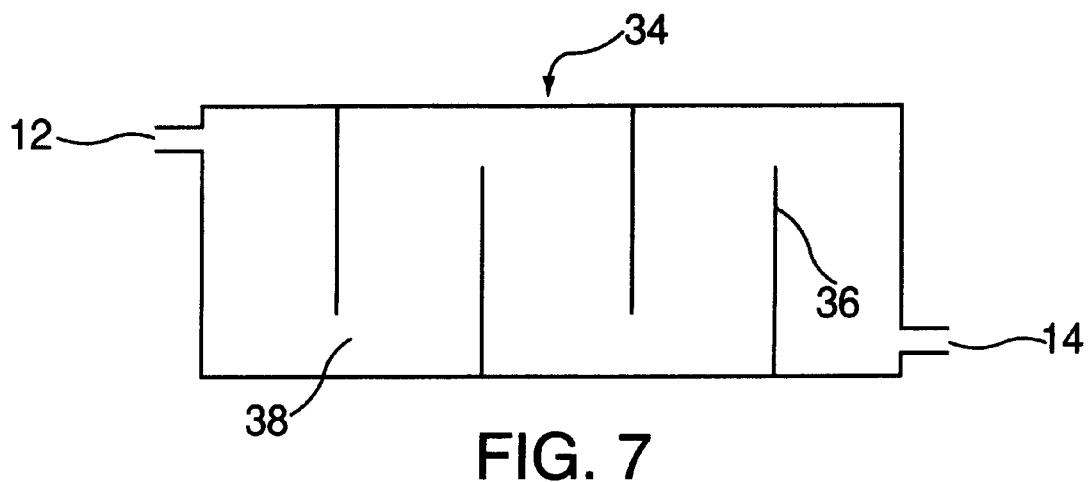
FIG. 7 is a cross-sectional top view of a reactor for use in a preferred embodiment of this invention having baffles.

Many aspects of the present invention will be better understood by those of skill in the art by reference to the figures. Referring to FIGS. 1 and 2, the numeral 10 indicates a reactor for use in the process of this invention. In the process, an aqueous waste stream containing one or more pollutants is introduced into reactor 10 via inlet 12, passes through reactor 10 (and exits the reactor via exit 14) in the presence of a gas comprising an effective amount of oxygen at a rate sufficient to reduce the concentration of at least one of the pollutants in the effluent stream to the desired levels. Reactor 10 contains a plurality of biologically active support materials as identified in FIGS. 1 and 2 by the numeral 16. As depicted in FIG. 3, biologically active support materials 16 comprise a support 18, having one or more types of a particulate adsorbents 20 for at least one of the pollutants contained in said aqueous stream on the surface of substrate 18 in the micropores of substrate 18 or on the surface of support 18 and in the micropores of substrate 18. Biologically active support materials 16 also include one or more types of microorganism 22 on, in or on and in substrate 18 and/or adsorbent 20 which are capable of metabolizing at least one of the materials contained in the waste stream.

Although a biological treatment can be carried out using aerobic or anaerobic microorganisms, aerobic processes are preferred since aerobic systems work at a faster rate than anaerobic. The process is carried out in the presence of a gas comprising an effective amount of oxygen. As used herein, an "effective amount of oxygen" is an amount of oxygen which is sufficient to supply the metabolic requirement oxygen for the micro-organisms metabolizing the target pollutant. It is important that reactor 10 be oxygenated to provide the necessary amount of oxygen for proper microbial metabolism and pollutant degradation. The amount of oxygen required in any situation will vary widely and will depend to a significant extent on the requirements of the particular microorganism(s) employed in the process and other factors known to those of skill in the art. In general, the amount of oxygen distributed in the process feed stream is at least about 2 mg of oxygen per liter of aqueous feed. In the preferred embodiments of the invention, the amount of oxygen is from about 2 mg/L of feed to about 10 mg/L of feed, and in the most preferred embodiments of the invention, the amount of the oxygen is from about 6 mg/L of feed to about 8 mg/L of feed. In the preferred embodiments of this invention, the gas is distributed uniformly or substantially uniformly throughout all or a portion of the biologically active biomass. The manner in which the gas is introduced into reactor 10 may vary widely. The gas may be introduced into reactor 10 employing conventional methods. For example, in the vertical or up-flow reactor of FIG. 1, the gas is introduced into reactor 10 with the aqueous feed stream at the bottom of the reactor through use of sparger 24 which introduces the gas in the form of small diameter gas bubbles. Supplemental gas can be introduced, if required, at various points along the vertical length of reactor 10 (not depicted in the drawing). In a embodiment of the invention in which reactor 10 is a horizontal reactor, as for example the reactor of FIG. 2, the gas can be introduced along the horizontal length of reactor 10 at various points to achieve a substantially uniform distribution of the gas in the feed stream in reactor 10. In this embodiment, the up-flow of the gas is orthogonal or substantially orthogonal to the direction of the flow of the aqueous feed stream. In the most preferred embodiments of the invention, reactor 10 is in a horizontal configuration in which the gas is distributed uniformly or substantially uniformly throughout all or substantially all of reactor 10. In these most preferred embodiments, the gas is introduced into reactor 10 along the horizontal length of reactor 10 as depicted in FIG. 2. In this mode, a more uniform distribution of the gas in the feed stream is achieved.

Process temperatures may vary widely and will depend on the particular microorganisms chosen for use. In general, the process is carried out at a temperature sufficiently high so as to not unduly interfere with the metabolism of the microorganism and sufficiently low as not to promote heat inactivation of the microorganism. Process temperatures are usually from about 5° C. to about 65° C. Process temperatures are preferably in the range of from about 15° C. to about 65° C., more preferably in the range of from about 12° C. to about 45° C. and most preferably in the range of from about 25° C. to about 35° C.

The aqueous pollutant-containing stream is treated in the process of this invention for a time sufficient to reduce concentration levels of at least one pollutant in the effluent stream the desired extent. In general, with aqueous feed streams in which the concentration levels of at least one pollutant is equal to or less than about 5000 ppm a hydraulic residence time of less than about 48 hours, preferably less than about 24 hours, and more preferably less than about 15 hours, suffices to reduce the concentration of at least one pollutant in the effluent stream to a concentration equal to or less than bout 22 parts per million (ppm), preferably equal to or less than about 10 ppm, more preferably equal to or less than about 1 ppm and most preferably equal to or less than about 0.1 ppm, with a concentration of equal to or less than about 0.02 ppm being the concentration of choice. The particular hydraulic residence time depends upon the amount of pollutant material in the feedstock, operating temperature, the presence of other materials in the feedstock, the density of microorganisms in the fixed bed, and so forth.

The aqueous waste streams which may be treated using reactors containing the biomass supports of this invention and the pollutants contained in such streams may vary widely. Waste streams containing inorganic (e.g. ammonia) or organic materials can be treated. The organic materials include a vast number of hydrocarbons and modified hydrocarbons, such as aliphatics, aromatics, heteroaromatics and halogenated derivatives thereof. Additional organic pollutants include hydrocarbons which contain functional groups, for example, a hydroxy, aldehyde, carboxylic acid, cyano and sulfur-containing groups ($-SO_3H$, $-SO_4$, $-S-$, SH, and _SR wherein R is a monovalent hydrocarbon). One of the major classes of organic pollutants consists of aromatic hydrocarbons, such as benzene, toluene, xylenes, alkylbenzenes, phenolic materials and halogenated derivatives thereof as well as polynuclear aromatic hydrocarbons such as naphthalene, anthracene, chrysene, acenaphthylene, acenaphthene, phenanthrene, fluorene, fluoranthene, naphthacene, pyrene and halogenated derivatives thereof (e.g. polychlorinated biphenyls, hexachlorobenzene, 5-bromouracil, 2,4-dichlorophenol and so forth). In the preferred embodiments of this invention, the pollutants are those which are common in waste streams from industrial manufacturing facilities. For example, phenolic materials are preferred pollutants for treatment in the process of this invention. Illustrative of phenolic materials are phenol, cresols, resorcinols, catechol, halogenated phenols as for example, 2-chlorophenol, 3-chlorophenol, 4-chlorophenol, 2,4-dichlorophenol, pentachlorophenol, nitrophenols such as 2-nitrophenol and 4-nitrophenol, and 2,4-dimethyl-phenol. Phenolic materials are found in waste streams of phenol manufacturers, of phenol users, of phenol resin producers, of coal tar processing facilities, and of wood pulping plants and other facilities practicing delignification. This is not to say that the process can or must be practiced only on such streams. The process which is the invention herein may be practiced on any aqueous feed containing levels of organic pollutants which are to be reduced.

The initial concentration of pollutants contained in the aqueous waste stream used in the process of this invention may vary widely. One of the advantages of this invention relative to prior art bioremediation processes is that waste streams containing relatively high amounts of pollutants can be treated. The concentration of organic pollutants in process streams treatable in the process of this invention are "biologically treatable levels" As used herein, "biologically treatable levels" are pollutant concentrations which do not inhibit or excessively inhibit the metabolism of the pollutants by the microorganism. Effluent streams from industrial processes such as phenol manufacturing plants and coal tar processing plants may have pollutant levels in excess of 20,000 ppm which may interfere with the process. It is preferred to reduce these levels to biologically treatable levels through use of conventional procedures such as solvent extraction, steam distillation and the like. In general, the concentration of pollutants in the aqueous streams is equal to or less than about 5000 ppm. Obviously, the lower concentration is not critical and does not represent a limitation on the process. In the preferred embodiments of this invention, the concentration of organic pollutants is equal to or less than about 4000 ppm, and in the particularly preferred embodiments of the invention the concentration of pollutants is equal to or less than about 3000 ppm. Amongst these particularly preferred embodiments of the invention, most preferred are those in which the concentration of pollutants is equal to or less than about 2000 ppm with a pollutant concentration of equal to or less than about 800 ppm being the concentration level of choice. Obviously, with a longer hydraulic retention time, greater concentrations of pollutants can be biologically treated.

The pH of the pollutant-containing feed may need to be adjusted for optimum biodegradation. In general, the pH is within the pH range allowing metabolism of the target pollutant(s). In the preferred embodiments of the invention, the pH of the feed is from about 6 to about 9, and in the most preferred embodiment of the invention, the pH of the feed is from about 6.5 to about 7.5.

Nutrients may need to be provided. Such materials may be added through use of known additives such as fish meal peptone, soybean flour, peanut oil, cotton seed oil, and the like, and usually salts capable of providing phosphate, sodium, potassium, ammonium, calcium, sulfate, chloride, bromide, nitrate, carbonate or like ions may be required. Trace elements known to those skilled in the art may be added as required. Usually sufficient amounts often are present in the aqueous feed to satisfy minimum requirements of the microorganism.

The aqueous feed stream is introduced into reactor 10 employing conventional means and is passed through reactor 10 employing an "effective hydraulic retention time" As used herein, an "effective hydraulic retention time" is a time which is sufficient for the process to reduce the concentration of pollutants in the effluent stream to the desired levels. Hydraulic retention times may vary widely and in general depend on such factors as the concentration of pollutants in the aqueous feed stream, desired maximum concentration of pollutants in the aqueous effluent stream, the microorganisms contained in the biomass, the pollutant, and the like. An advantage of the process of this invention is that reductions in pollutant concentration can be obtained with relatively short hydraulic retention times. In the preferred embodiments of this invention hydraulic retention times are equal to or less than about 48hrs, and in the particularly preferred embodiments of the invention such times are from about 10 to about 36 hrs. Amongst these particularly preferred embodiments of the invention, most preferred are those embodiments in which the hydraulic retention time is from about 10 to about 24 hrs.

As noted, one advantage of the process of this invention is that the process is resistant to upset by relatively high concentrations of pollutant(s) in the influent stream. When the concentration of a pollutant in an influent stream is increased from a first concentration, $C_1$, to a second higher concentration, $C_2$, for a period of 1 HRT, the increase to $c_2$ causes an increase in the concentration of the effluent stream. In our process the concentration of said pollutant in the effluent stream is reduced to less than about 0.15 $C_2$ within about 1/24 HRT or less after the end of flowing through a reactor an influent stream at concentration $C_2$ for said 1 HRT. In addition, the process provides that upon decreasing the concentration of pollutant in the influent to $C_1$ and maintaining the concentration of pollutant at or about the $C_1$ level for at least one HRT, the concentration of pollutant in the effluent stream decreases to less than or equal to about 0.12 $C_1$ within about 1 HRT or less. For example, when there is a two-fold increase in the pollutant concentration from $c_1$ to $C_2$, wherein $c_1$ is a pollutant concentration level less than the level at which microorganisms are inhibited, the treatment process is able to reduce the pollutant concentration in the effluent stream at less than 0.15 $c_2$ within 1/24 of the selected HRT for the process. Preferably, the process can reduce the pollutant concentration to such levels when $c_2$ is a concentration at which the microorganisms would otherwise be at least partially inhibited.

In additional embodiments of this invention, the purification process is such that the concentration of pollutant in the effluent stream in response to an increase of pollutant concentration in the influent from $C_1$ to $C_2$ for 1 HRT is reduced to less than or equal to about 0.075 $C_2$ within about 1/24 HRT at the end of said 1 HRT at $C_2$ and upon returning the influent pollutant level to $C_1$ and maintaining at $C_1$ for at least 1 HRT, the concentration of pollutant in the effluent decreases to less than or equal to about 0.001 $C_1$ within about 1 HRT or less.

More preferably, in the purification process of this invention, the concentration of pollutant in the effluent stream, in response to an increase of pollutant concentration in the influent stream from $C_1$ to $C_2$ for 1 HRT, is reduced to less than or equal to about 0.01 $C_2$ within about 1/24 HRT at the end of said HRT at $C_2$ and upon decreasing influent pollutant level from $C_2$ back to $C_1$, and maintaining at $C_1$, for at least 1 HRT, the concentration of pollutant in the effluent stream decreases to less than or equal to about 0.001 $C_1$ within about 1 HRT or less.

In further preferred embodiments of the purification process of this invention, the concentration of pollutant in the effluent stream in response to an increase of pollutant concentration in the influent from $C_1$ to $C_2$ for 1 HRT is reduced to less than or equal to about 0.005 of $C_2$ within about 1/24 HRT or less at the end of said HRT at $C_2$ and upon decreasing the influent pollutant level from $C_2$ back to $C_1$ and maintaining the concentration of pollutant at or about $C_1$ for at least 1 HRT, the concentration of pollutant in the effluent stream decreases to less than or equal to about 0.0005 $C_1$ within 1 HRT or less.

The embodiments of this invention establish purification processes which can significantly reduce pollutant levels in the effluent of a reactor in spite of an occasional "shock" to the biological system of a relatively high pollutant level in the influent and often maintain the effluent pollutant concentration below EPA mandated levels. "Shock" refers to a change in the concentration of pollutant in the influent stream of about 500 to 5,000 parts per million over a relatively short time (usually ranging from 1 hr up to a 1–2 days). Important to obtaining a purification process which is resistant to shock (often referred to as resistant to upset) of relatively high pollutant levels in the influent stream is the choice of biologically active support materials and components used therein. One of the main objectives of the invention is to provide a support material having an effective amount of active adsorbent on a substrate for use in a biological waste treatment reactor which achieves government mandated level of pollutant effluent and an ability to resist upset of the treatment system. The biomass supports of this invention comprise a substrate on the surface of which is firmly adhered an adsorbent. For porous supports, the adsorbent is situated on any exposed surface, including inner pores of a porous structure, such as an open-celled foam. The biomass supports are placed in a bioreactor. In a process for purification of a waste stream by biodegradation, the waste feed stream containing one or more pollutants is passed through the bioreactor, which is generally pretreated with pollutant-degrading microorganisms.

The novel aspects of this invention relate to biomass supports and unique processes which result from the use of the supports in reactors for biological waste treatment. When used in a biological treatment process, the biomass supports of this invention provide treatment processes which are resistant to upset.

It is theorized that the ability of a support to produce the process of this invention, said process being resistant to upset as discussed above, is related to the alpha value for the particular support. An alpha value is calculated based on the formula below:

$$\text{alpha value} = \frac{\frac{[g \text{ pollutant removed from solution}]}{[g \text{ support}]}}{\frac{[g \text{ pollutant remaining in solution}]}{[g \text{ solvent in which pollutant is carried}]}}$$

The alpha value reflects the ability of the support (per gm) to remove pollutant from solution. The alpha value is measured using a set volume of a particular pollutant (100 ppm pollutant in 100 ml solution) in water or other solvent for the pollutant and measuring the initial pollutant concentration and the final pollutant concentration after the support is placed in the solution for a set time, usually about 24 hours. The pollutant concentration in solution at the end of the 24 hours is measured to obtain an alpha value for the support. For the process of this invention, the support used should have an alpha value (per gram of support, said support comprising a substate, an adsorbent and optionally, a binder) of at least about 100. Preferably, the alpha value for the support is at least about 200. More preferably, the alpha value is at least about 400. In further preferred embodiments, the alpha value is at least about 600. In particularly preferred embodiments, the alpha value is at least about 1,000. In more particularly preferred embodiments, the alpha value is at least about 1500. In alternative embodiments, the alpha value is at least about 2,000, with the alpha value of choice being greater than about 3,000.

The biomass supports of this invention can be produced by several varied processes, such as heat treatment, solvent-slurry and binder attachment. A support for use as a biomass support comprises a substrate and an adsorbent which is attached or firmly adhered to the substrate via one of the above processes.

Figure 10:
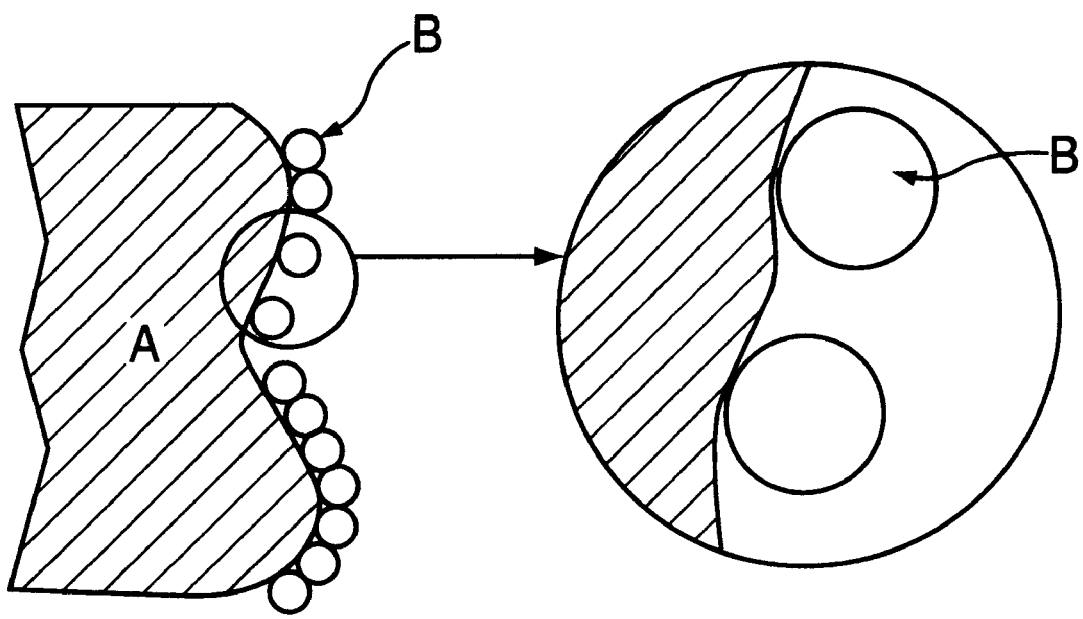
FIG. 10 is a diagram of a support having a monolayer of adsorbent particles on the surface of the support.

In heat treatment process, a substrate is heated to a temperature at which it softens during which time carbon is mixed with the substrate material, which is allowed to cool. Upon cooling the adsorbent is adhered/affixed on the substrate surface. An effective temperature must be selected in order that the adsorbent is not deactivated by heat treatment. Temperatures and heating time will vary with the choice of substrate and adsorbent. Generally, a support is heated in the presence of an adsorbent at a temperature of at least about 50° C. for at least about 1 hour. The support produced by the heat treatment process creates an essentially monophasic layer of adsorbent particle, at the surface of the support (See FIG. 10).

In another embodiment of the invention, biomass supports are prepared by using a solvent-slurry of adsorbent (especially, activated carbon). The solvent/adsorbent slurry can be applied to the substrate using conventional techniques. Preferably, the substrate is dipped in the slurry or spray coated with the slurry and then dried. It is important that the adsorbent be affixed firmly to the substrate in an active state after any excess slurry is removed from the support. It should be noted that although we refer to the method as "solvent slurry", the solvent merely functions as a solution for dispersing the adsorbent in a fluid matrix or may soften the substrate surface and/or swell the substrate. After coating the substrate with the slurry, the solvent may be evaporated and recycled. Similar to the heat treatment process, the solvent-slurry method also creates a monophasic layer of adsorbent particles on the surface of the support since the solvent is substantially removed by conventional drying techniques. Some of the solvent may remain on the adsorbent and/or support which requires the selection of a solvent which does not de-activate the adsorbent's ability to bind a pollutant.

Although the solvent slurry method produces a substrate with active adsorbent deposited thereon, there may be some tendency for the adsorbent material to leach out from the substrate over time. As long as a substantial amount of adsorbent remains in the reactor, preferably near the support materials, and does not flow out in the effluent, the biomass support produced by the solvent-slurry method can continue to be useful as a biomass support.

Generally, for the solvent slurry, the selection of solvent may vary widely. The solvent can be selected from water or hydrocarbons, such as alcohols, esters, ethers, ketones, amines and nitrated or halogenated hydrocarbons. Solvents which may be used in the practice of this invention include water, alcohols, such as methanol, ethanol, propanol, isopropanol and ethylene glycol; ketones, such as acetone, methylethyl ketone, cyclohexanone and butyrolactone; as well as acetates, such as methyl acetate, ethyl acetate, propyl acetate and butyl acetate. Additional solvents include nitromethane, nitroethane, tetrachloroethane, chloroform, benzene, toluene, chlorobenzene, xylene, n-butyl chloride, cyclohexane, ethylene carbonate, propylene carbonate, dimethyl acetamide, dimethyl formamide, dimethyl sulfoxide, acetonitrile, hexamethylphosphoramide, n-methylpyrrolidone, tetrahydrofuran, diethylether formic acid and derivatives thereof.

Preferably, the solvent employed is a non-aromatic solvent. Especially in the case of treating aromatic pollutants such as phenols, aromatic solvents tend to inhibit the amount of phenol bound by the adsorbent.

The more preferred embodiments of the invention are directed to the use of an effective binder to attach the adsorbent to the substrate. An effective binder is a material which is capable of binding an adsorbent to the surface of a substrate such that there is no or substantially no loss of adsorbent into the effluent of the bioreactor and there is no or substantially no deactivation of the adsorbent by the binder. Specifically, an effective binder is selected such that the purification process is resistant to upset. Partial coating of the support is acceptable as long as the process remains resistant to upset. The binder may be selected from any type of binder known in the art, e.g. in the particulate binding art, pigment binding art or powder binding art. Examples of binders are water soluble polymers which can be crosslinked or polymerized into water insoluble forms such as natural gums, cellulose and starch derivatives, salts of alginic acids and polymers and copolymers of acrylic acid, acrylamide, vinyl alcohol and vinyl pyrrolidone. Examples of useful organic binders which are soluble in organic solvents include cellulose esters, cellulose ethers, polymers and copolymers of vinyl esters such as vinyl acetate, acrylic acid esters, and methacrylic acid esters, vinyl monomers such as styrene, acrylonitrile and acrylamide, and dienes such as butadiene and chloroprene; natural rubber and synthetic rubber such as styrene-butadiene.

There is a tendency for binders to decrease the efficiency of an adsorbent by diminishing the adsorbent's capacity or by interfering with a pollutant's access to the adsorbent, e.g. binder envelops the adsorbent. It is theorized that disadvantages associated with an adsorbent/binder support system can be at least partially compensated by employing binders that possess a greater degree of free volume. Free volume ($V_f$) is releated to the fluidity and mobility of the constiuitive polymer chains and is a measure of the volume through which small molecules can migrate. Free volume is the difference between the specific volume of the polymer mass (v) and the volume of the solidly packed molecules. Basically, the free volume of the is the volume of the polymer mass not actually occupied by the molecules themselves.

Presently, the Tg, glass transition temperature, is known to be correlative to free volume (for discussion of free volume and Tg, see Stephen L. Rosen *Fundamental Principles of Polymeric Materials,* Chap. 8, "Transitions in Polymers", pp.89–95, 1982). Rosen theorizes that the more free volume in a polymer, the lower the $T_g$. Therein, Tg is used to correlate the structure of the binder to its ability to function as an effective binder in a biomass support system. In preferred embodiments of this invention an effective binder has a Tg less than or equal to about 100° C. In more preferred embodiments, the effective binder has a Tg less than or equal to about 50° C. In further preferred embodiments, an effective binder has a Tg less than or equal to about 30° C. In particularly preferred embodiments, an effective binder has a Tg less than or equal to 20° C. In more particularly preferred embodiments, an effective binder has a Tg less than or equal to about SAC. In alternative embodiments, the preferred binder has a Tg of less than or equal to about 10° C. with the binder of choice having a Tg of less than or equal to about 25° C.

As previously noted, the affinity of the support system for pollutants, such as phenolic materials, is related to the Tg. In many instances, the Tg can be lowered by increasing the polarity and/or hydrophilicity of the polymer binder used in the support system. Any conventional method of increasing the hydrophilicity or polarity of a polymer can be used to improve such properties of a binder material. For example, many polymers, including homopolymers and copolymers, can be rendered more hydrophilic and/or more polar by (1) carboxylation along the polymer backbone (e.g. carboxylated styrene butadiene), carboxylation of side chains and functional groups and (3) by introducing -COOH containing monomers as comonomers in the polymer binder. Each of the above should lower the Tg of polymers.

In alternative embodiments of this invention, an effective binder is solvent suspendable or dispersable in that once the binder and solvent are mixed, the mixture forms a stable dispersion of binder. It is noted that the binder should be soluble in a non-aromatic solvent, if a solvent is needed, since an aromatic solvent may inactivate some adsorbents as previously discussed. Once the adsorbent is applied and dried, the binder should be substantially water-insoluble for use in a waste stream treatment process and should not degrade in the environment of the bioreactor. The binder also should not excessively inhibit the binding of pollutants. Many commercial binders (e.g. adhesives) are produced and sold as dispersions. In preferred embodiments, the binder is water-suspendable for application to the substrate and water-insoluble once cured on a substrate. An example of solvent-suspendable binders are what is known in the art as a latex. Generally, a latex is a solvent-suspendable form (liquid-in-liquid), which is stabilized by surface active agents. Although the methods of applying an adsorbent and a binder to substrate can vary widely, applicant prefers the following two methods since the support materials produced thereby have a significantly high level of affinity for pollutants.

Figure 11:
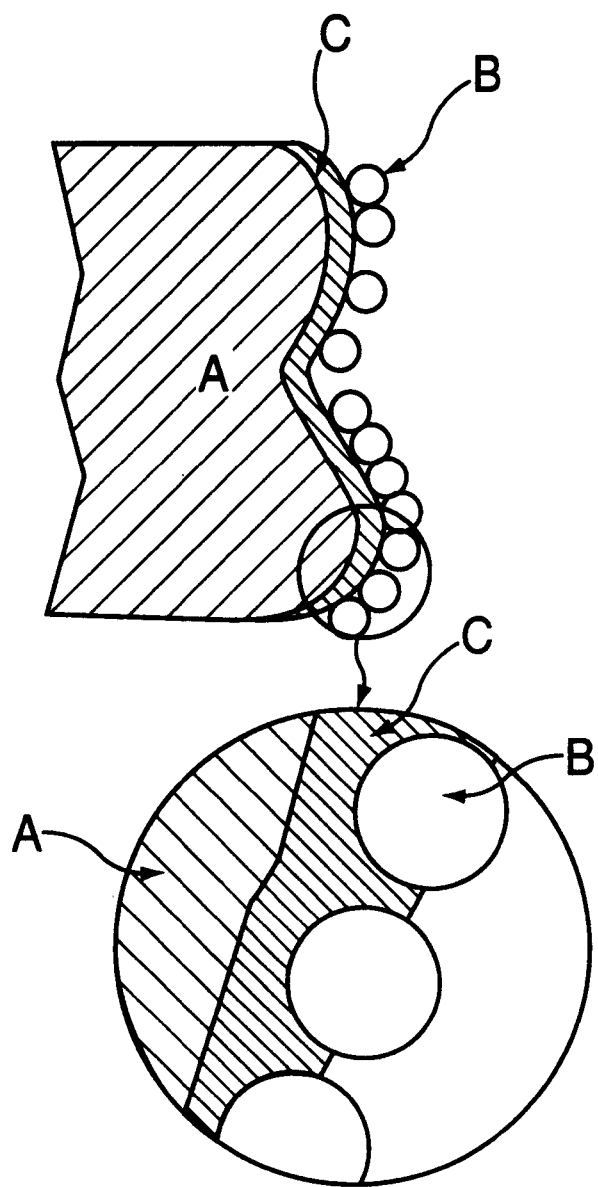
FIG. 11 is a diagram of a support haing thereon a layer of binder to which is attached a layer of adsorbent articles.

The first method, which is referred to as the "two step" method, comprises (i) applying a layer of an effective binder to the surface of a substrate; (ii) then adding one or more adsorbents onto the binder/substrate surface and (iii), optionally, allowing the binder to cure until it becomes tacky prior to applying the adsorbent. The time for curing in step (iii) will vary for each binder employed. For many binders, the preferred curing time is 0. Once the adsorbent is applied, the binder is allowed to dry to a solid or semi-solid material. The drying time needed to solidify the binder will vary for each binder selected. The two-step method creates a support material having three distinct single phase layers of component. The first layer is a substrate, the second is the binder and the third is a layering of adsorbent particles on the binder as depicted in FIG. 11. Since the adsorbent is substantially only on the surface of the binder of the support, the selection of binder can vary widely to include virtually any binder that will bind the adsorbent firmly; however, preferred are the effective binders of this invention.

Figure 12:
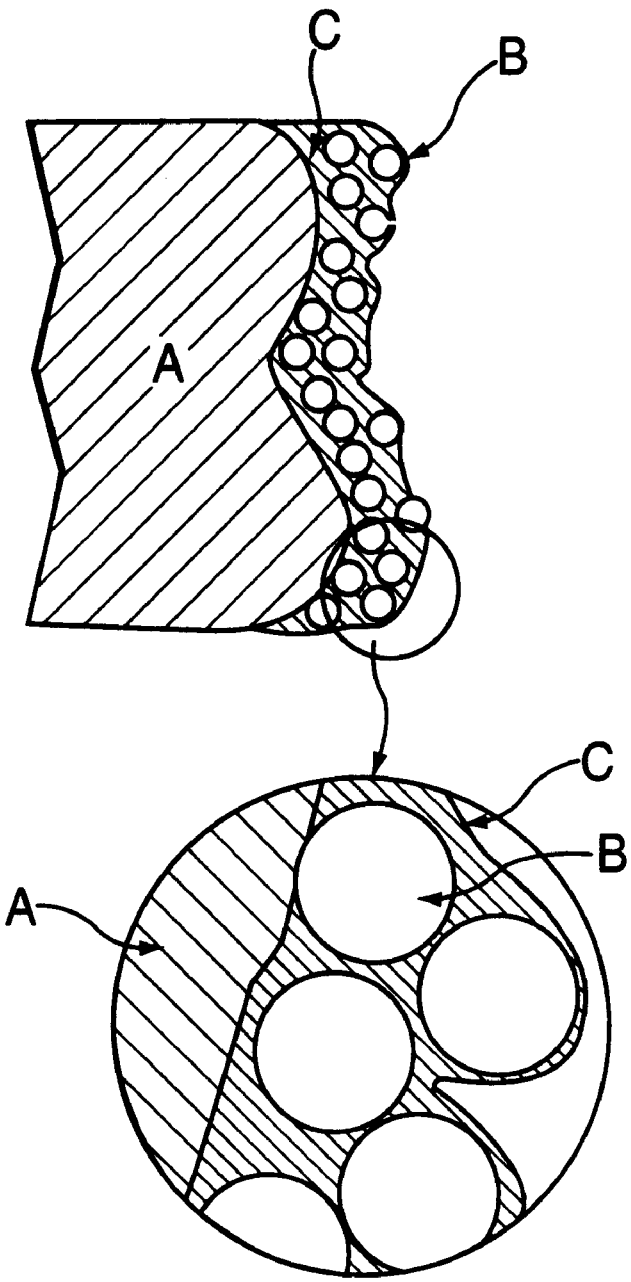
FIG. 12 is a diagram of a support having a two-phase of adsorbent dispersed in the binder.

Another preferred method of making the support materials of this invention comprises (i) applying a slurry coating which comprises a binder, an adsorbent and solvent for the binder, to a substrate; and (ii) allowing the slurry coating to dry. The slurry application of binder and adsorbent creates a bi-layer support of a substrate and a second two phase layer of adsorbent dispersed in the binder or in and on the binder (See FIG. 12). Because the slurry method produces the second matrix layer in which the adsorbent is dispersed throughout a binder, the binder may often envelop the adsorbent. Therein, the binders employed in preferred embodiments are those possessing a greater degree of free volume in order to preserve a substantial amount of the activity of the adsorbent and permit sufficient interaction of the pollutant with adsorbent such that when the support is used in a bioreactor the purification process is resistant to upset.

Additives, such as surfactants and dispersants, can be added to the slurry to obtain a more uniform dispersion of adsorbent and binder in the solvent such that and the slurry can be applied evenly to the substrate.

The amount of binder used in the practice of the invention will vary with the amount and structure of the substrate as well as the amount of adsorbent to be bound. Generally, the amount should both substantially cover the substrate and bind the adsorbent. It is noted that excess binder not only can substantially decrease the actual size of inner pores of a substrate but also require additional amounts of additives for forming an adequate slurry. Furthermore, a greater thickness of binder enveloping the adsorbent will tend to inhibit or mitigate the adsorbent's pollutant binding properties. The presence of excess additives, e.g. surfactants, may deactivate an adsorbent.

The novel biomass supports of this invention can be used in conventional biological waste treatment systems, such as continuous stirred reactors, fixed-bed reactors and fluidized-bed reactors. Preferably, a fixed-bed reactor system is employed in the practice of this invention to provide a treatment process with low sludge production. Conventional fixed-bed systems are described in U.S. Pat. 4,983,299 to Lupton et al. which is incorporated herein by reference.

Absorbent 20 for use in the practice of this invention may vary widely. The adsorbent, e.g. activated carbon, once bound to the substrate should function as a solid state buffer adsorbing excess pollutant within the reactor when the pollutant concentration is increased and releasing pollutant into solution when concentration decreases. The buffering effect is described by a series of on and off constants ($K_{on}$ and $K_{off}$), each reflecting the affinity of a particular site on the adsorbent for the particular pollutant. The ratio of $k_{off}/k_{on}$ equals $K_D$, which reflects the affinity of the adsorbent for a pollutant. At equilibrium, the number of molecules of pollutant that are binding to the adsorbent is equal to the number of molecules of pollutant leaving the adsorbent and entering the solution. Basically, for the process of this invention the adsorbent, once bound to the substrate or substrate and binder or binder, has a bound phase that is in sufficiently rapid equilibrium with the solution such that pollutants in solution resulting from a 1 HRT increase in the concentration of pollutants in the influent stream are bound within about 1/24 HRT after the end of said increase to maintain a desired level of pollutants in the effluent stream. The the pollutant should also be released into solution at a rate sufficient to allow microbial degradation of the pollutant upon return to a concentration equal to or less than about $C_1$. The desired level of pollutants in the wastestream per day or per month is usually dictated by the EPA. The desired level of pollutants in the effluent stream will also dictate the response time required for a treatment process to adsorb an increase of pollutants in the wastestream. Generally, the response time should be at least less than about 1 HRT. In other words, if a influent stream having pollutant concentration $C_2$ above a first influent stream flows through a reactor for a period of 1 HRT, e.g. 24 hours, the support media should be able to adsorb a substantial portion of the excess pollutant in the reactor (and, in conjunction with the degradative action of the microbes, return the pollutant concentration in the effluent to the level prior to the increase to $C_2$) within at least about 24 hours from the time of the end of the 1 HRT at the higher pollutant concentration. Preferably, the response time is less than or equal to about 1/3 HRT. More preferably, the response time is less than or equal to about 1/6 HRT. In particularly preferred embodiments, the response time is less than or equal to about 1/8 HRT. In more particularly preferred embodiments, the response time is less than about 1/12 HRT, with the most preferred being less than or equal to about 1/24 HRT.

The only requirement of the adsorbent 20 of this invention is that it is capable of adsorbing the target pollutant on its surface and is capable of binding or being bound to the substrate surface by a number of mechanisms such as surface compatibility, charge and by a binding polymer such as polypropylene (See U.S. Pat. No. 4,089,609, col. 4, lines 14 to 30).

Illustrative of useful materials for use in the fabrication of adsorbent 20 are carbons such as coal, carbon black, activated carbon, and activated charcoal, silica gel, active clays, zeolites, hydrophobic and ion exchange resins, molecular sieves, and the like. In the preferred embodiments of the invention, adsorbent 20 is formed from carbons such as coal, charcoal, carbon black and activated carbon, and in the particularly preferred embodiments of the invention, the particulate adsorbent is formed from activated carbon. However, it will be clear to a person skilled in the art that any other particulate material can be used to form adsorbent 20 may be used. The activated carbon which is preferably used may be produced by heat treatment of vegetable matter, animal matter, coal, lignite, petroleum residues or synthetic organic polymers either with or without the addition of chemicals, and is characterized by rapid and effective adsorption of the targeted pollutants.

Adsorbent 20 is in particulate form and is preferably porous to provide for greater surface area. The preferred particulate adsorbent 20 has a surface area at least about 500 $m^2/g$, preferably at least about 700 $m^2/g$, and is preferably of a size such that at least about 70% of the adsorbent particles are smaller than about 44 microns. That is, a minimum of about 70% of the adsorbent particles pass through a 325 mesh sieve. In the preferred embodiments of the invention, powdered adsorbent 20 has as high a pore volume as is practical, more preferably at least about 0.5 $cm^3/g$, and most preferably at least about 0.7 $cm^3/g$, with as great a porosity as possible contributed by pores preferably of greater than about 1 micron in size. Maximization of the macropores maximizes the concentration of microorganisms in the immediate proximity of the surface of adsorbent 20. Powdered adsorbent 20 used in the practice of the preferred embodiments of this invention have a surface area of from about 700 to about 2000 $m^2/g$, a pore volume of from about 0.7 to about 1.0 $cm^3/g$, with from about 70 to about 100% of the particles being under 44 microns in size. Although these correspond to characteristics of commercially available material, the invention per se imposes no such limitations and materials having as high a surface area as possible are the materials of choice.

The amount of adsorbent employed may vary widely and depends on a number of factors including the specific activity of adsorbent for the target pollutant. In the preferred embodiments of the invention, the amount of adsorbent is an amount which is at least sufficient to maintain a steady state of an amount of the target pollutant which will allow the microorganism to metabolize the pollutant in the required time period to provide an effluent stream having less than about 22 ppm of the target pollutants. In the more preferred embodiments of the invention, the amount of adsorbent is from about 5 weight percent to about 85 weight percent on a dry basis and based on the total weight of substrate, binder and adsorbent. In the particularly preferred embodiments of the invention, the amount of adsorbent is from about 10% by weight to about 50 weight percent on a dry basis and based in the total weight of substrate, binder and adsorbent, and in the most preferred embodiments of the invention, the amount of adsorbent is from about 20% by weight to about 40% by weight on the aforementioned basis.

Microorganism 22, used in the practice of this invention, are anaerobic and aerobic microorganisms selected to degrade target pollutants in ways well known in the art. The microorganisms can be employed as a pure strain or as a consortium of microorganisms. In preferred embodiments of the invention, aerobic microorganisms are employed. Although anaerobic microorganisms often degrade pollutant materials at a slower rate than aerobic microorganism, an anaerobic process may be required to degrade a pollutant or an intermediate product to a material which is susceptible to aerobic degration to a non-toxic level or to a non-pollutant material. For example, ammonia can be remediated anaerobically first and then aerobically to the final products. Useful microorganisms 22 may vary widely and may be naturally occurring microorganisms 22 or may be genetically engineered microorganisms 22. The only requirement is that microorganisms 22 are capable of metabolizing the target pollutant(s) to the required effluent levels over the required period of time. In the preferred embodiments of the invention, microorganisms 22 are obtained from the pollutant-containing waste stream or from soil which has been in contact with the waste stream.

In the operation of the process, the cell content of microorganisms 22 (including extracellular proteins produced by microorganisms) is an amount which is sufficient to reduce the organic pollutant content to the desired concentration level within the desired hydraulic retention time. In the preferred embodiments of the invention, cell content of microorganisms 22 is at least about 0.3% by weight based on the total weight of microorganisms 22, substrate, binder and adsorbent 20, and in the most preferred embodiments of the invention is from about 0.3% by weight to about 15% by weight based on the aforementioned basis. Among these particularly preferred embodiments most preferred are those embodiments in which the cell content of microorganisms 22 is from about 0.5 to about 10% by weight based on the total weight of adsorbent 20, microorganisms 22 and substrate 18, with a content of from about 0.8 to about 5% by weight on the aforementioned basis being the amount of choice.

Substrate 18 used in the practice of this invention is in particulate form. The size and shape of substrate 18 can vary widely. For example, substrate 18 may be in particulate form of regular shape such as tubular, rod shaped, rectangular, spherical, hexagonal or the like, or may be of irregular shape. The particle size may vary widely and is preferably at least from about 0.10 in. More preferred particle sizes are from about 0.2 in. to about 12 in., and most preferred particle sizes are from about 0.50 in. to about 6 in. with a particle size of from about 0.50 in. to about 3 in. being the particle size of choice.

In the preferred embodiments of the invention, where all or a portion of microorganisms 22 and adsorbent 20 are incorporated in substrate 18, substrate 18 is preferably an open cell material having a relatively high macro porosity, as for example a foam. This allows the pollutant-containing aqueous feed to flow through the interior of the substrate. In the preferred embodiments of the invention, substrate voids are at least about 0.2 millimeters, and preferably the voids range about 0.2 mm to about 5 to about 6 millimeters in size. Substrate 18 also needs to be resistant to the shear forces and abrasion present in a fixed bed reactor, and should have good crush strength. In these preferred embodiments of the invention, substrate 18 is preferably semi-flexible, with a density of under about 2 pounds per cubic foot for optimum economic feasibility. However, higher density substrates, of from about 4 to about 5 pounds per cubic foot or even higher, are usable. It should be realized that substrate density is related to the economics of the invention and not to its performance; the invention may be practiced with a large range of substrate densities, even if certain ranges may present distinct economic advantages.

The material used to form substrate 18 is not critical and may vary widely. The only requirements are that the material does not degrade when contacted with binder, solvent, wastestream or microorganisms; that it has a degree of affinity for the binder and/or adsorbent of choice and the substrate does not inhibit the properties of the adsorbent and/or binder.

Illustrative of useful materials for fabrication of substrate 18 are ceramics such as bentonite, kaolinite, kieselguhr, diatomaceous earth, alumina, silica, zirconia, barium titanate, synthetic carbides, synthetic nitrides and synthetic borides and the like. Illustrative of still other materials which can be used in the fabrication of substrate 18 are glasses such as soda-lime-silica glasses, lead glasses, borosilicate glasses, laser glasses, silica glasses, and glass-ceramics.

Illustrative of still other useful substrate materials are synthetic and naturally occurring polymeric materials such as polyamides such as poly(hexamethylene adipamide) (nylon 66), poly(4-aminobutyric acid) (nylon 4), poly(6-aminohexanoic acid) (nylon 6), poly(hexamethylene sebacamide) (nylon 6,10) and the like; polyesters such as poly(ethylene terephthalate), poly(butylene terephthalate), poly(1,4-cyclohexane dimethylene terephthalate) and the like; polyolefins such as polyethylene, polypropylene, poly (4-methyl pentene), polystyrene and the like; polyvinyls such as polyvinyl alcohol, poly(vinyl methyl ether), poly (vinyl methyl ketone), poly(vinyl pyrrolidone) and the like; polyacrylics such as polyacrylic acid, polymethacrylic acid, poly(methyl acrylate) poly(methyl methacrylate) poly acrylonitrile, polyacrylamide, poly(methacrylamide) and the like. Other useful polymeric materials for use in the fabrication of the polymeric substrate are polyurethanes such as those derived from reaction of diisocyanates such as toluene diisocyanates, diphenyl methane diisocyanates, hexamethylene 1, 6-diisocyanate, dicyclohexylmethane diisocyanate, 1,5-naphthalene diisocyanate, p-phenylene diisocyanate, m-phenylene diisocyanate, 2,4-toluene diisocyanate, 4,4'diphenylmethane diisocyanate, 3,3'-dimethyl-4, 4'diphenylmethanediisocyanate, 3,3'-dimethyl-4,4'biphenyl diisocyanate, 4,4'-diphenylisopropylidiene diisocyanate, 3,3'-dimethyl-4,4'-diphenyl diisocyanate, 3,3'-dimethyl-4,4'-diphenylmethane diisocyanate, 3,3'-dimethoxy-4,4'-biphenyl diisocyanate, dianisidine diisocyanate, tolidine diisocyanate, hexamethylene diisocyanate, 4,4'-diisocyananodiphenylmethane and the like and diols such as glycerin, trimethylolpropane, 1,2,6-hexane triol, methyl glycoside pentaerythriol, sorbital sucrose, ethylene glycol, diethylene glycol, hydroxy terminated polyesters formed by direct esterification of dicarboxylic acid with an excess of a disfunctional alcohol such as poly(tetramethylene adipate), poly(ethylene adipate), poly(1,4-butylene adipate), poly(1, 5-pentylene adipate), poly(1,3 butylene adipate), poly (ethylene succinate), poly(2,3-butylene succinate), polyether diols such as those prepared by reaction of a compound having active hydrogens such as di alcohols, poly alcohols, di phenols, polyphenols, aliphatic diamines or polyamines and aromatic diamines or polyamines with alkylene oxides such as styrene oxide, butylene oxide, propylene oxide, epichlorohydrin or mixtures of these alkylene oxides.

In the preferred embodiments of this invention, substrate 18 is formed from open-celled polyurethanes, such as cross-linked polymeric materials which can be foamed with an appropriate foaming agent such as nitrogen, helium, carbondioxide, azodicarbonamide and the like, to form open celled foams having the void characteristics described above. In these preferred embodiments of the invention, substrate 18 can be prepared and foamed in the presence of the selected microorganism without adversely affecting same.

In the particularly preferred embodiments of the invention, substrate 18 is formed from open-celled polyurethanes such as cross-linked poly-urethane-hydrogels. Such materials can be obtained from commercial sources or prepared in accordance with known techniques. For example, such materials may be obtained by reacting isocyanate prepolymers with water (in which diamines or polyamines are optionally contained as chain lengthening agents), or as cross-linking agents or by reacting a suitable polyol with a suitable diisocyanate or polycyanate reagent. Suitable polyols include long chain aliphatic diols and polyoxyalkylene ethers. The isocyanate prepolymers have isocyanate end-groups and are prepared by reacting poly oxyalkylene ethers with an excess of diisocyanate or polyisocyanates. Illustrative of useful polyoxyalkylene ethers are those which have a molecular weight of from about 500 to about 10,000, preferably from about 2,000 to about 8,000, which have at least two active hydrogens and which contain at least 30% by weight based on the total weight of the polyethers of oxyethylene groups. Other useful oxyalkylene groups include oxypropylene, oxybutylene and the like. Polyethers of this type are produced by reacting compounds which have reactive hydrogen atoms such as dialcohols, polyalcohols, diphenols, polyphenols, aliphatic diamines, aliphatic polyamines, aromatic diamines, or aromatic polyamines with a suitable alkylene oxide such as ethylene oxide, propylene oxide, butylene oxide, styrene oxide and the like. Suitable diisocyanates include toluene 4,4'-diisocyanate, toluene 2,4-diisocyanate, toluene 2,2-diisocyanate, diphenylmethane 4,4'-diisocyanate, diphenylmethane 2,4'-diisocyanate, diphenylmethane 2,2'-diisocyanate, toluene 2,6-diisocyanate, hexamethylene 1,6-diisocyanate and useful diamines and polyamines include aliphalic, cycloaliphatic and aromatic di- and polyamines such as ethylene diamine, hexamethylene diamine, diethylene triamine, hydrazine, guanidine, carbonate, N,N'-diisopropylhexamethylene diamine, 1,3-bisaminomethylbenzene, N,N'-bis-(2-aminopropyl)ethylene diamine, N,N'-(2-aminoethyl)ethylene diamine, 4,4'-diaminodiphenyl methane, 4,4'-dimethylamino-3,31-dimethyldiphenyl methane, 2,4'-diamino-diphenylmethane, 2,4-diaminotoluene, 2,6-diaminotoluene and the like.

The amount of substrate 18 included in the biologically active particles 16 may vary widely. In general, the amount of substrate 18 is from about 5 to about 40 weight percent based on that total weight of biologically article particle 16. In the preferred embodiments of the invention, the amount of substrate 18 is from about 10 to about 30 weight percent based on the total weight of particle 16, and in the particularly preferred embodiments is from about 10 to about 20 weight percent on the aforementioned basis.

Biologically active particle 16 may include various optional ingredients such as a material having cationic groups. Illustrative of such materials are standard ion exchange resins which have cationic groups or other polymers which have structures containing positively-charged nitrogen atoms such as polyaminocarboxylic acid esters having cationic groups, polyacrylamides having cationic groups, polyethylene imines having cationic groups, copolymers of acrylonitrile, styrene and dimethylaminoethyl methacrylate having cationic groups, and condensation products of diethylene triamine and maleic anhydride having cationic groups, copolymers of isobutylene and maleic anhydride, followed by imidization with specific diamines, having cationic groups. The content of polymers having cationic groups in the composition according to the invention may vary widely and is usually from about 0.2 to about 20% by weight based on the total weight of the biologically active particle, preferably from about 0.5 to about 15% by weight, and most preferably from about 1 to about 10% by weight, based on the total weight of the reaction mixture for the preparation of the composition. Illustrative of other optional components which can be used in the practice of this invention are density-increasing substances such as barite, metal powder, powdered rubber, clay powder, pumice powder, glass powder, powder obtained from the kernels and shells of olives and nuts, and rock-flour; density-reducing substrates such as small polystyrene globules, wood powder, powder from plastic waste, hollow microbeads, and polyethylene foam flakes; coloring agents such as coloring pigments, and dyes; short fibers of an organic or inorganic base such as glass fibers and gel-forming macromolecular substances such as types of cellulose, alginates, starch, and carrageenans.

The most preferred polymeric substrate material in the present invention is a flexible open-celled foam with a high permeability to water. The foam used in the practice of this invention must accommodate feed flow in a reactor. To this end, it is important that the foam has a highly interconnected porosity where the foam voids desirably are at least about 0.2 millimeters and can range up to about 10 millimeters or more in size.

An additional advantage provided by using a binder to affix adsorbent on a substrate is that the substrate can be pre-treated with a stiffening agent prior to treatment with a binder. Often in biological waste treatment process, a porous substrate, e.g. semi-flexible or flexible foams, may have a tendency to be compressed by the pressures generated during operation of the bioreactor, especially in a fixed-bed reactor. When compressed, the available surface area of the biomass support is decreased and performance of the reactor can be hindered. The amount of compression of the porous substrate can be reduced by coating the porous substrate with a stiffening agent. The stiffening agent can be selected from any conventional binder material. Since the stiffening agent does not necessarily interact with the adsorbent or pollutant many materials are available. In some instances, an effective binder may be sufficient to improve the rigidity of the substrate and improve resistance to compression without the need for pretreatment of the substrate with a separative stiffening agent.

Following attachment of activated carbon to the support, the biomass support so produced is then cut, as needed, into an appropriate size and loaded into a reactor. Alternatively, the coating of the substrate can be performed on pieces of the size to be used in the bioreactor. A suspension of pollutant degrading microbes is then added to the reactor. The biodegradative microbes adsorb and attach on, in or on and in the porous supports through natural processes well known in the art.

The following examples are merely illustrative and representative of our invention which is of considerably larger scope. These examples should not be considered limiting in any way.

EXAMPLE 1

Experiments were conducted to assess the abilty to bind activated carbon to a support by heat treatment.

General Method for Preparation of Support by Heat Treatment

1. Weigh 1"×1"×1" piece of PUF (polyurethane foam). The foam is ScottBlue Foamex(SBF) available from Foamex. It is a reticulated foam having 15–20 pores per inch.

2. Place excess (approx. 2 gm) PAC, type C powdered activated carbon available from Calgon, with SBF in a vessel, which is heated for various times at various temperatures while shaken.

3. Remove coated SBF from the vessel. Excess PAC was removed by shaking by hand and then washing with deionized water.

The amount of coverage of PAC was determined visually by observing the PAC covered SBF under a light microscope. The results are set forth in Table I.

TABLE I

PERCENT COVERAGE OF SCOTT BLUE FOAMEX WITH PAC SUBSEQUENT TO HEATING AT VARIOUS TEMPERATURES AND SHAKING FOR VARIOUS TIMES.

| EXPT NO | TEMP ° C. | TIME, HRS | % COVERAGE | COMMENT |
|---|---|---|---|---|
| −1 | 23 | 24 | 45 | A |
| −2 | 94 | 1 | 30 | " |
| −3 | 94 | 4 | 70 | " |
| −4 | 94 | 24 | 90 | " |
| −5 | 23 | 24 | 45 | B |
| −6 | 94 | 1 | 20 | " |

TABLE I-continued

PERCENT COVERAGE OF SCOTT BLUE FOAMEX WITH PAC
SUBSEQUENT TO HEATING AT VARIOUS TEMPERATURES
AND SHAKING FOR VARIOUS TIMES.

| EXPT NO | TEMP ° C. | TIME, HRS | % COVERAGE | COMMENT |
|---|---|---|---|---|
| −7 | 94 | 4 | 60 | " |
| −8 | 120 | 1 | 35–40 | A |
| −9 | 120 | 4 | 65–70 | " |
| −10 | 120 | 24 | 95 | " |
| −11 | 120 | 24 | 95 | " |
| −12 | 137 | 1 | 65 | " |
| −13 | 137 | 4 | 95 | " |
| −14 | 137 | 24 | 99 | " |
|  |  |  | 40* | C |

A- SBF was used as received.
B- SBF was washed in deionized water prior to applying PAC.
C- The same procedure as experiment 14, except that the PAC covered SBF was subjected to an additional vigorous washing in deionized water.

Summary of Experiments in Table I

In experiments 1–7, where the sample was heated at 94 deg C for from 1 to 24 hrs., only small quantities of PAC were bound, less than 0.02 g PAC per g SBF. As the treatment time increased from 1 to 24 hrs., microscopic investigation of the foam surface indicated coverage increased from about 30 to about 90%. Treatment at higher temperatures around 70 to 137 deg C. (experiments 8–14) yielded progressively higher % coverage (see table I) such that after 24 hrs at virtually 99% was obtained. Weight gains of about 2–8% were obtained. The heat method suffered from a lack of tight binding of the PAC to the PUF but maintained the PAC in an active state. During heat treatment, water was driven from the PAC. Basically, temperatures from about 70 to about 137 deg C. appeared to aid binding of the PAC to PUF. Shaking removes minimal amounts of PAC while vigorous washing in deionized water removes more than 60% of the PAC.

Binding Activity Measurements

In order to evaluate a number of support systems without using each in a bioreactor, alpha values were used to analyze relative binding characteristics of the supports prepared. For each sample, the alpha value is calculated using the alpha value formula as previously described.

The alpha value can vary significantly based on the amount of adsorbent and amount of initial pollutant (e.g. phenol) used. However, the differences of the alpha value for the same amount of initial phenol can be correlated to the relative effectiveness of the support to bind a pollutant. The correlation is validated by the results obtained in the bioreactor (ICB) experiments. The general procedure for the alpha value determination is as follows:

1. A 1"×1"×1" (or similarly dimensioned) cube or slab of the material to be assayed for it's ability to bind phenol was either formed as a composite or cut from a larger piece of material/composite.

2. Into a wide mouth 250 Pyrex flash (No. 5100) was added 100 ml of 100 ppm phenol (+/−about 2% by assay) using a No. 3022 Pyrex 100 ml graduated cylinder.

3. The top of the flask was fitted with an aluminum foil-covered No. 8 rubber stopper. The function of the aluminum foil is to prevent organics from being adsorbed by the stopper.

4. The cube of material to be tested was added to the phenol solution, the mouth of the flask sealed with the stopper, and the flask agitated on an orbital shaker at 250 RPM for 24 hours.

Solutions were assayed for phenol as follows:

Measurement of Pollutant Concentration

The 4-aminoantipyrine (AAP) standard analytical method was used for measuring phenol concentration. See Standard Methods for Examination of Water and Wastewater, 16th ed (1985), Method (510-4AAP). For measurements of samples having less than 1 ppm phenol, a separate standard curve employing phenolic concentrations between 0.25 and 1 ppm was used. In some examples the amount of pollutant was determined using GC/MSD which stands for gas chromatographic analysis with mass selective detector. The GS/MSD is both more sensitive and discriminatory than the 4-AAP method.

EXAMPLE 2

Using the heat treatment method and phenol assay described above, an alpha value was calculated. The PAC and SBF were heated for 24 hours at a temperature of 100° C. The results are provided in the table below.

TABLE II

DETERMINATION OF ALPHA VALUES FOR BINDING
OF PHENOL BY COMPOSITE

| Initial Phenol CONC. PPM | FINAL Phenol CONC. PPM | SUPPRT Weight GM | ALPHA Value |
|---|---|---|---|
| 107.5 | 72.51 | 0.417 | 115.7 |
| 107.5 | 71.12 | 0.561 | 91.23 |

For the above experiment and each experiment for determining an alpha value, the phenol is placed in water and the vol.=100 ml.

EXAMPLE 3

Determining the Effect of Solvent on Alpha Value of PAC 1.0 g PAC and 100 ml of a particular solvent were placed into a 250 ml erlenmeyer flask and were agitated on an orbital shaker for 24 hours. The PAC was collected on filter paper and allowed to dry overnight at room temperature. One tenth gram of exposed PAC was then mixed with 100 ml of a 100 ppm solution of phenol in water in a 250 ml erlenmeyer flask and shaken at 100 RPM for 5 hours on the orbital shaker. The results of the assay of phenol in supernatant infraction are shown in Table III.

As can be seen by the alpha values (a small number shows PAC deactivated) the non-aromatic solvents had an insignificant negative effect on the ability of PAC to remove phenol from solution.

TABLE III

DEACTIVATION OF PAC WITH VARIOUS SOLVENTS WITH NO SUPPORT: ALPHA VALUES FOR BINDING OF PHENOL TO PLAIN PAC

DEACTIVATION OF PAC WITH DIFFERENT SOLVENTS

| SOLVENT | INITIAL PHENOL CONC. PPM | FINAL PHENOL CONC. PPM | ALPHA VALUE |
|---|---|---|---|
| 1 WATER | 96.9 | 23.840 | 3065.4 |
| 2 METHANOL | 96.9 | 22.220 | 3361.8 |
| 3 ACETONE | 96.9 | 22.510 | 3305.6 |
| 4 ETHANOL (ABS) | 96.9 | 22.680 | 3273.4 |
| 5 ETHANOL (3A) | 96.9 | 23.250 | 3168.6 |
| 6 ETHYL ACETATE | 96.9 | 29.640 | 2269.9 |
| 7 XYLENE | 96.9 | 74.140 | 307.3 |
| 8 NO SOLVENT, FRESH PAC | 96.9 | 20.690 | 3684.4 |
| 9 PHENOL | 96.9 | 96.9 | 0.0 |

VOLUME = 100 ML
PAC WEIGHT = 0.100 in each solvent experiment above.

The following examples and Tables were obtained using the materials and method described herein. The alpha values generated reflect improvements in the application of the binder to a substrate or the benefit of a specific binder or solvent as noted.

Materials

Polyurethane foams employed in the experiments were Scott Blue Polyurethane foam (SBF) available from Foamex and a 13000 Series foam available from General Foam.

Activated carbon available for Calgon

Consumer Adhesives
(available at most hardware stores)
Minwax Liquid Polyurethane,
Diamond Varathane (water soluble liquid polyurethane)
Sunnyside brand linseed oil
Elmer's glue (water based polyvinyl acetate adhesive).

Commercial Adhesives

Airflex 465, obtained as about 66% min solids, water born emulsion of ethylene-vinyl acetate copolymer, with a $T_g$ (glass transition temperature) of –3° C., was obtained from Air Products and Chemicals Inc.

Synthemul 40404-00, obtained as a 55 to 57% solids, polyvinyl alcohol stabilized (PVA) carboxylated acrylic copolymer latex emulsion, with a $T_g$ of –50 (onset) to –42° C. (inflection), was obtained from Reichold Chemicals.

Elvace 40722-00, obtained as a 55 to 57% solids, hydroxyethyl cellulose stabilized ethylene-vinyl acetate copolymer latex water emulsion, with a $T_g$ of about –8 to 14° C., was obtained from Reichold Chemicals.

Tylac 68219-00, obtained as a 51 to 53% solids, PVA stabilized styrene-butadiene copolymer latex water emulsion, with a $T_g$ of –25 (onset) to –11° C. (inflection), was obtained from Reichold Chemicals.

Polysat EVSA, obtained as a 50% solids, styrene and vinyl toluene modified acrylic copolymer in a an organic solvent containing xylene, was obtained from Polysat Inc. ($T_g$ not disclosed by Polysat). Polysat SAE, obtained as a 45% solids, styrene acrylate copolymer emulsion in water AR-100 solvent suspension was also obtained from Polysat ($T_g$ not disclosed).

Polymethylmethacrylate (PMMA-catalog no. 18221-4), polystyrene (MW=45 K) and polystyrene (MW=280 K) were all purchased from Aldrich Chemical.

In Examples 4–10, supports were prepared using two-step procedure in applying the adsorbent and binder to the support. The objective is to assess the alpha value of supports employing different binders. The alpha value is also shown for the support having just binder and no adsorbent (PAC). In each experiment, the foam used in the PUF (Polyurethane Foam), SBF from Foamex.

RE: TABLES

A shorthand method for describing the different supports was employed. The sequence of shorthand abbreviations described the sequence of addition of the components of the support and which binder was employed. For example, PUF/Lo/16HR/PAC/DAYS/HEAT means PUF was coated with Linseed Oil (Lo), allowed to dry (tack time) for 16 hours, coated with PAC by shaking linseed oil coated PUF with PAC, allowed to air cure for 2–3 days, and then heated 1 hour. The support is then assayed for its ability to remove phenol from solution.

General Method of Preparation of Supports for Determining Phenol Binding Using Adhesives Our "two step" approach, where the liquid is first coated onto the substratum (PUF) and then the PAC is bound, as follows:

1. Weigh a 1"×1"×1" piece of PUF.
2. Soak in the fluid 1–2 min. The fluid is 50:50 adhesive/solvent dispersion. The solvent for the binder is generally water, except as noted.
3. Remove excess fluid first by squeezing and then by blowing with compressed nitrogen gas for 30 sec.
4. Place in jar with excess PAC (about 5 g) and shake vigorously for 15 min.
5. Shake off excess PAC.
6. Air cure for time as noted.
7. Dry in oven 2 h at 100° C. as noted.

EXAMPLE 4

Consumer adhesives, linseed oil, Minwax Liquid Polyurethane, Diamond Varathane and Elmer's Glue were used to screen potential materials for use as binders. As shown in Tables III, IV and V, only the Elmer's glue, a water-based polyvinyl acetate adhesive proved to be of significant value, with relatively high alpha values. The Diamond Varathane was solvent based and was believed to contain organic solvents that would de-activate the PAC. A similiar solvent effect may be occuring for the inseed oil and Minwax.

TABLE IV

BINDING OF PAC TO PUF USING LINSEED OIL (LO) OR MINWAX (MW)
ALPHA VALUES FOR BINDING OF PHENOL BY COMPOSITE:

| SAMPLE | INIT PHENOL CONC. PPM | FINAL PHENOL CONC. PPM | SUPPRT WEIGHT GM | ALPHA VALUE |
|---|---|---|---|---|
| 1 PUF | 107.5 | 71.12 | 0.561 | 91.23 |
| 2 PUF/LO | 107.5 | 74.13 | 1.144 | 39.37 |
| 3 PUF/LO/ 16 HR/PAC | 107.5 | 62.39 | 1.622 | 44.57 |
| 4 PUF/MW | 107.5 | 81.71 | 0.855 | 36.92 |
| 5 PUF/ MW/PAC | 107.5 | 60.51 | 1.170 | 66.36 |
| 6 PHENOL CONTROL | 107.5 | 107.5 | | |

TABLE IV-continued

BINDING OF PAC TO PUF USING LINSEED OIL (LO) OR MINWAX (MW)
ALPHA VALUES FOR BINDING OF PHENOL BY COMPOSITE;

| SAMPLE | INIT PHENOL CONC. PPM | FINAL PHENOL CONC. PPM | SUPPRT WEIGHT GM | ALPHA VALUE |
|---|---|---|---|---|
| 7 LOOSE PAC | 107.5 | 1.43 | 0.250 | 29586 |
| 8 PUF/MW/ 1 HR/PAC | 107.5 | 80.83 | 1.344 | 24.55 |
| 9 PUF/MW 1 HR/PAC HEAT | 107.5 | 88.67 | 1.095 | 19.40 |

EXCEPT FOR No. 3, ALL HEATING OF SAMPLES PERFORMED FOR A PERIOD OF ONE HR @ 100°, TIME BEFORE "PAC" IS TACK TIME & "HEAT" AFTER, "PAC" DENOES THE ADDITION OF CURE STEP.

TABLE V

BINDING OF PHENOL TO PAC COATED LIQUID POLYURETHANES/SCOTT BLUE FOAMEX

ALPHA VALUES FOR BINDING OF PHENOL BY COMPOSITE

| SAMPLE | INITIAL PHENOL CONC. PPM | FINAL PHENOL CONC. PPM | SUPPORT WEIGHT GM | ALPHA VALUE |
|---|---|---|---|---|
| 1 PUF/MW/PAC | 120.2 | 95.60 | 0.773 | 33.29 |
| 2 PUF/DiV/PAC | 120.2 | 59.96 | 0.827 | 121.44 |
| 3 PUF/DiV/PAC | 120.2 | 47.59 | 0.798 | 191.20 |
| 4 PUF/DiV/30 MIN/ PAC | 120.2 | 49.62 | 0.890 | 159.89 |
| 5 PUF/DiV/60 MIN/ PAC/HEAT | 120.2 | 49.13 | 0.941 | 153.73 |
| 6 PUF/DiV/PAC/ HEAT | 120.2 | 67.08 | 1.022 | 77.52 |
| 7 PUF/DiV/30 MIN/ PAC/HEAT | 120.2 | 40.14 | 1.046 | 190.75 |

MW = MINWAX; DiV = DIAMOND VARATHANE

TABLE VI

BINDING OF PAC TO PUF USING POLYVINYL ACETATE (ELMER'S GLUE): ALPHA VALUES FOR BINDING OF PHENOL BY COMPOSITE.

BINDING OF PAC TO SCOTT BLUE FOAMEX WITH ELMER'S GLUE

PHENOL BINDING STUDIES.

| SAMPLE | INITIAL PHENOL CONC. PPM | FINAL PHENOL CONC. PPM | SUPPORT WEIGHT GM | ALPHA VALUE |
|---|---|---|---|---|
| 1 PUF/EG | 108.6 | 68.4 | 0.5588 | 104.9 |
| 2 PUF/EG/PAC | 108.6 | 6.77 | 0.8850 | 1700.1 |
| 3 PUF/EG/PAC | 108.6 | 12.0 | 0.8519 | 949.4 |
| 4 PUF/EG/15/PAC | 108.6 | 4.64 | 0.9202 | 2434.3 |
| 5 PUF/EG/30/PAC | 108.6 | 30.0 | 0.6513 | 403.2 |
| 6 PUF/EG/ PAC/HEAT | 108.6 | 28.9 | 0.6253 | 441.2 |
| 7 PHENOL | 108.6 | 108.6 | | |

VOL = 100 ml; EG = ELMER'S GLUE
Samples 2, 4, & 5 show that the tack time (i.e. drying of binder before adding PAC) can effect the alpha value.

It should be noted that the alpha values can vary substantially with the number of grams of support. In addition, each support is manually prepared so there is a degree of variance attributed to human error.

EXAMPLE 5

In this example, the two-step procedure was used to prepare supports using a variety of commercial adhesives as listed in the materials section above. Many of the adhesives are latexes, which obviate any problem of de-activation of PAC by organic solvents. The performance for each for each is easily obtained by reviewing sample no. 3 in each of Tables VII, VIII and IX.

TABLE VII

BINDING OF PAC TO PUF USING COMMERCIAL ETHYLENE POLYVINYL ACETATE (AIRFLEX 465): ALPHA VALUES FOR BINDING OF PHENOL BY COMPOSITE. BINDING OF PAC TO SCOTT BLUE FOAMEX PUF USING COMMERCIAL ETHYLENE POLYVINYL ACETATE (AIRFLEX 465); EFFECT OF TACK TIME AND HEAT: ALPHA VALUES FOR BINDING OF PHENOL BY COMPOSITE.

| SAMPLE | INITIAL PHENOL CONC. PPM | FINAL PHENOL CONC. PPM | DELTA PHENOL CONC. PPM | SUPPORT WEIGHT GM | INITIAL PHENOL/ GM SUPPORT | ALPHA VALUE |
|---|---|---|---|---|---|---|
| 1 PUF/AF | 104.0 | 75.9 | 28.1 | 0.5941 | 175.1 | 62.3 |
| 2 PUF/AF/HEAT | 104.0 | 76.5 | 27.5 | 0.5691 | 182.7 | 63.2 |
| 3 PUF/AF/PAC | 104.0 | 8.2 | 95.8 | 0.9529 | 109.1 | 1226 |

TABLE VII-continued

BINDING OF PAC TO PUF USING COMMERCIAL ETHYLENE POLYVINYL ACETATE (AIRFLEX 465): ALPHA VALUES FOR BINDING OF PHENOL BY COMPOSITE. BINDING OF PAC TO SCOTT BLUE FOAMEX PUF USING COMMERCIAL ETHYLENE POLYVINYL ACETATE (AIRFLEX 465); EFFECT OF TACK TIME AND HEAT: ALPHA VALUES FOR BINDING OF PHENOL BY COMPOSITE.

| SAMPLE | INITIAL PHENOL CONC. PPM | FINAL PHENOL CONC. PPM | DELTA PHENOL CONC. PPM | SUPPORT WEIGHT GM | INITIAL PHENOL/ GM SUPPORT | ALPHA VALUE |
|---|---|---|---|---|---|---|
| 4 PUF/AF/PAC/HEAT | 104.0 | 20.7 | 83.3 | 0.7010 | 148.4 | 574 |
| 5 PUF/AF/30/PAC | 104.0 | 23.0 | 81.0 | 0.6935 | 150.0 | 508 |
| 6 PUF/AF/30/PAC/HEAT | 105.0 | 12.16 | 92.8 | 0.7281 | 144.2 | 1049 |
| 7 PUF/AF/60/PAC | 105.0 | 9.63 | 95.4 | 0.7738 | 135.7 | 1280 |
| 8 PUF/AF/60/PAC/HEAT | 1O5.0 | 12.85 | 92.15 | 0.7181 | 146.2 | 999 |

ASSAY VOL = 100.0 ML; AF = AIRFLEX ADHESIVE; ADHESIVE DILUTED 50%, V/V, WITH WATER.

TABLE VIII

BINDING OF PAC TO PUF USING A STYRENE ACRYLIC POLYMER (POLYSAT EVSA-X-VM & P, DILUTION OF ONE PART ADHESIVE WITH ONE PART ACETONE): ALPHA VALUES FOR BINDING OF PHENOL BY COMPOSITE. BINDING OF PAC TO SCOTT BLUE FOAMEX USING POLYSAT EVSA ALPHA VALUES FOR PHENOL BINDING TO COMPOSITE

| EXPT NO | SAMPLE | INITIAL PHENOL CONC. PPM | FINAL PHENOL CONC. PPM | SUPPRT WEIGHT GM | ALPHA VALUE |
|---|---|---|---|---|---|
| 1 | PUF/PS/0 | 99.8 | 74.9 | 1.1986 | 27.6 |
| 2 | PUF/PS/0/HEAT | 99.8 | 77.7 | 1.2069 | 23.5 |
| 3 | PUF/PS/0/PAC | 99.8 | 53.0 | 1.7296 | 51.1 |
| 4 | PUF/PS/0/PAC/HEAT | 99.8 | 58.7 | 1.4712 | 47.6 |

VOLUME = 100 ML, PS = POLYSAT EVSA-X-VM & P ADHESIVE.
The above results show that aromatic solvents inhibit binding since the commercial adhesive as purchased is believed to contain aromatic solvents. The $T_g$ of the binder may be acceptable.

TABLE IX

BINDING OF PAC TO PUF USING CARBOXYLATED ACRYLIC COPOLYMER LATEX (SYNTHEMUL 40404-00:ALPHA VALUES FOR BINDING OF PHENOL BY COMPOSITE. BINDING OF PAC TO PUF USING SYNTHEMUL. ALPHA VALUES FOR PHENOL BINDING.

| SAMPLE | INITIAL PHENOL CONC. PPM | FINAL PHENOL CONC. PPM | DELTA PHENOL CONC. PPM | SUPPORT WEIGHT GM | INITIAL PHENOL/ GM SUPPORT | ALPHA VALUE |
|---|---|---|---|---|---|---|
| 1 PUF/SYN | 101.2 | 74.496 | 26.692 | 0.5982 | 169.2 | 59.9 |
| 2 PUF/SYN/HEAT | 101.2 | 74.920 | 26.268 | 0.5704 | 177.4 | 61.5 |
| 3 PUF/SYN/PAC | 101.2 | 2.495 | 98.693 | 0.8636 | 117.2 | 4580.4 |
| 4 PUF/SYN/PAC/HEAT | 101.2 | 3.945 | 97.243 | 0.7205 | 140.4 | 3421.2 |
| 5 PUF/SYN/30 MIN/PAC | 101.2 | 4.705 | 96.483 | 0.7880 | 128.4 | 2602.3 |
| 6 PUF/SYN/30 MIN/PAC/HEAT | 101.2 | 2.814 | 98.374 | 0.8301 | 121.9 | 4211.4 |
| 7 PUF/SYN/60 MIN/PAC | 101.2 | 7.286 | 93.902 | 0.8716 | 116.1 | 1478.7 |
| 8 PUF/SYN/60 MIN/PAC/HEAT | 101.2 | 3.892 | 97.296 | 1.0126 | 99.9 | 2468.8 |
| 9 PUF/SYN/60/PAC/UNDIL | 101.2 | 9.637 | 91.551 | 1.1894 | 85.1 | 798.7 |

ASSAY VOL = 100 ML; PUF = SCOTT BLUE FOAMEX; SYN = 50% (V/V) SYNTHEMUL ADHESIVE.

EXAMPLE 6

This example investigated the ability of an agent to siffen the PUF foam in order to improve resistance to compression when used in a bioreactor, especially a fixed bed reactor.

Each of substrates, 2 General Foam and 2 SBF cubes of 1"×1"×1" size, were dipped in Minwax and squeezed several times until no air bubbles came out, then removed from the Mixwax and shaken until no Minwax was seen coming off. The cubes were heated in a vacuum oven at 60° C. for about 6 days to remove traces of organic solvents. The cubes were then treated following the normal two-step procedure.

The results (shown in the table below) indicate that the selection of stiffening agent can include any binder. For a relatively high alpha value, the binder used to atach the adsorbent to the support is important. The two-step procedure was employed, except that a stiffening agent was applied prior to the binder to which the adsorbent is adhered. The stiffening agent is allowed to cure for about 2 hours before applying the second binder.

TABLE X

BINDING OF PAC TO MINWAX STIFFENED FOAMEX USING 50% SYNTHEMUL:
ALPHA VALUES FOR PHENOL BINDING BY COMPOSITE.

| SAMPLE | INIT PHENOL CONC. PPM | FINAL PHENOL CONC. PPM | SUPPRT WEIGHT GM | ALPHA VALUE |
|---|---|---|---|---|
| 1 GENERAL FOAM | 100.0 | 0.756 | 1.4451 | 6870 |
| 2 GENERAL FOAM | 100.0 | 0.543 | 1.8377 | 5414 |
| 3 S.BLUE FOAMEX | 100.0 | 0.799 | 1.1530 | 8606 |
| 4 S.BLUE FOAMEX | 100.0 | 0.680 | 1.2116 | 8200 |

EXAMPLE 7

In this example, the two-step procedure was employed again; however, the commercial binder is Synthemul and the substrate General Foam Series 13000. The results below show the effect of increasing the pores/per sq. in. in a substate.

TABLE XI

BINDING OF PAC TO GENERAL FOAM USING SYNTHEMUL
ALPHA VALUES FOR PHENOL BINDING

| SAMPLE | INIT PHENOL CONC. PPM | FINAL PHENOL CONC. PPM | SUPPRT WEIGHT GM | ALPHA VALUE |
|---|---|---|---|---|
| 1 GF/SYN/0 | 101.6 | 78.651 | 0.8632 | 34 |
| 2 GF/SYN/0/HEAT | 101.6 | 74.933 | 0.8569 | 41 |
| 3 GF/SYN/0/PAC | 101.6 | 0.266 | 1.4213 | 26745 |
| 4 GF/SYN/0/PAC/HEAT | 101.6 | 0.224 | 1.7454 | 25931 |
| 5 GF/SYN/30/PAC | 101.6 | 0.306 | 1.3076 | 25341 |
| 6 GF/SYN/30/PAC/HEAT | 101.6 | 0.344 | 1.8201 | 16175 |
| 7 GF/SYN/60/PAC | 101.6 | 0.269 | 1.6304 | 23088 |
| 8 GF/SYN/60/PAC/HEAT | 101.6 | 0.253 | 1.5122 | 26524 |

VOL, ML = 100.0
Cure(tack) time = 0, 30 or 60 min as indicated.

EXAMPLE 8

This example examined the effect of heating a support once formed, washing a formed support and the effect of washing and heating a support once formed. See results in table below.

TABLE XII

TWO-STEP PROCEDURE BINDING OF
PAC TO WASHED GEN. FOAM USING 50% SYNTHEMUL.
ALPHA VALUE FOR PHENOL BINDING BY COMPOSITE

| SAMPLE | INIT PHENOL CONC. PPM | FINAL PHENOL CONC. PPM | SUPPRT WEIGHT GM AFTER | ALPHA VALUE |
|---|---|---|---|---|
| 1 GF/SYNTH/WASHED | 98.8 | 81.40 | 0.7128 | 30 |
| 2 GF/SYNTH/HEAT/WASH | 98.8 | 77.92 | 0.7505 | 36 |
| 3W GF/SYNTH/0/PAC/WASH | 98.8 | 2.65 | 1.3833 | 2619 |
| 3NW GF/SYNTH/0/PAC/NO WASH | 98.8 | 1.94 | 1.5615 | 3200 |
| 4 GF/SYNTH/0/PAC/HEAT/WASH | 98.8 | 8.96 | 1.4026 | 715 |
| 5 GF/SYNTH/30/PAC/WASH | 98.8 | 3.77 | 1.2727 | 1982 |
| 6 GF/SYNTH/30/PAC/HEAT/WASH | 98.8 | 13.34 | 1.2678 | 505 |
| 7 GF/SYNTH/60/PAC/WASH | 98.8 | 13.80 | 1.2196 | 505 |
| 8 GF/SYNTH/60/PAC/HEAT/WASH | 98.8 | 4.48 | 1.3124 | 1606 |

ASSAY VOLUME, ML = 100. SEQUENCE OF ADDITIONS FOR SAMPLE PREP: SOAK FOAM IN ADHSV, ALLOW ADHSV TO GET TACKY FOR 0, 30 or 60 MIN, +/− HEAT (1 HR @ 115 DEG. C.) AS INDICATED, BIND PAC TO SURFACE, +/− WASH (2 × 1 HR IN D.I. WATER) AS INDICATED.
ABREVIATIONS: GF = GENERAL FOAM, PAC = POWDERED ACTIVATED CARBON, ADHSV = SYNTH = SYNTHEMUL ADHESIVE.

The above data shows the significant negative effects of heating and insignificant effect of washing the support systems. It is noted that the washing is done by vigorously agitation of the support in deionized water. Heating the support at varioius stages in the preparation has a significant negative effect on the alpha value of the support.

EXAMPLE 9

This example examined the effect of varying the amount of adsorbent available for forming the support. Results are shown in the table below.

TABLE XIII

TWO-STEP PROCEDURE BINDING OF PAC
TO GENERAL FOAM USING 50% SYNTHEMUL AND VARIOUS AMT'S OF PAC. ALPHA VALUES FOR PHENOL BINDING TO COMPOSITE.

| SAMPLE NUMBER G PAC* | INIT PHENOL CONC. PPM | FINAL PHENOL CONC. PPM | SUPPRT WEIGHT GM AFTER | ALPHA VALUE |
|---|---|---|---|---|
| 1 2.5 | 100.4 | 0.698 | 1.6082 | 8885 |
| 2 2.5 | 100.4 | 0.414 | 1.3513 | 17879 |
| 3 1.25 | 100.4 | 0.830 | 1.3493 | 8896 |
| 4 1.25 | 100.4 | 0.804 | 1.4488 | 8550 |
| 5 0.83 | 100.4 | 0.796 | 1.4602 | 8565 |
| 6 0.83 | 100.4 | 1.464 | 1.2955 | 5217 |
| 7 0.5 | 100.4 | 1.905 | 1.0519 | 4915 |
| 8 0.5 | 100.4 | 0.988 | 1.1437 | 8801 |
| 9 0.25 | 100.4 | 10.24 | 0.9235 | 953 |

TABLE XIII-continued

TWO-STEP PROCEDURE
BINDING OF PAC
TO GENERAL FOAM USING 50% SYNTHEMUL AND VARIOUS
AMT'S OF PAC. ALPHA VALUES FOR PHENOL BINDING
TO COMPOSITE.

| SAMPLE NUMBER G PAC* | INIT PHENOL CONC. PPM | FINAL PHENOL CONC. PPM | SUPPRT WEIGHT GM AFTER | ALPHA VALUE |
|---|---|---|---|---|
| 10 0.25 | 100.4 | 7.19 | 1.0822 | 1198 |
| PHENOL CONTROL | 100.4 | 100.4 | | |

PUF CUBE DIMENSIONS = 1" × 1" × 1".
The above data shows the effects of decreasing the amount of PAC available for forming the support system.
*This is the amount of PAC employed step 2 of the two-step procedure. This number corresponds to the amount of PAC shaken with the wet, adhesive-coated PUF.

EXAMPLE 10

This example observed the effect of using a slurry method to apply a binder.

General Slurry Procedure

1. Weigh a 1"×1"×1" piece of PUF.

2. Prepare a slurry by diluting the adhesive in the described solvent (usually 50% adhesive and 50% solvent, (water) by volume), stirring rapidly using a magnetic stir bar and stir plate, and adding the described amount of PAC until the PAC is completely wetted by the diluted adhesive. The suspension is not always smooth and homogeneous, i.e., aggregation occurs. The stirring time is usually 5 to 10 min. A surfactant is added where noted to diminish aggregation.

3. Soak in the PAC/adhesive slurry for 1–2 min while squeezing to remove all entrapped air.

4. Remove the cube from the slurry and then excess fluid first by squeezing and by pressing against the side of the container. Quite often the slurry was lumpy. Any large lumps were scraped off of the sides of the cube prior to drying.

5. Dry in air, or heat in oven for 2 h at 100° C. (as described in individual experiments). When a short air drying time was used (<1 day) there was ofter milkiness in the supernatant of the phenol binding assay, indicating incomplete drying had occured. Milkiness was not observed when drying was for two or more days at room temperature.

TABLE XIV

SLURRY PROCEDURE
BINDING OF PAC/ADHESIVE
SLURRY TO PUF EMPLOYING EITHER SYNTHEMUL OR
POLYSAT AS ADHESIVE: ALPHA VALUES FOR BINDING
OF PHENOL BY COMPOSITE.

BINDING OF PAC TO BLUE FOAMEX USING
PAC/ADHESIVE SLURRY
ALPHA VALUES FOR PHENOL BINDING.

| SAMPLE | INITIAL PHENOL CONC. PPM | FINAL PHENOL CONC. PPM | SUPPRT WEIGHT GM | ALPHA VALUE |
|---|---|---|---|---|
| SYNTHEMUL SLURRY | 99.8 | 0.551 | 2.2792 | 7894 |
| POLYSAT SLURRY | 99.8 | 72.3 | 1.9101 | 20 |

VOL, ML = 100.0
Inactivation of the sample with Polysat (EVSA) is due to aromatic solvents in the commercial adhesive.

EXAMPLES CONTINUED

The substratum used in the most of the studies described below is General Foam 13000 series polyurethane foam (PUF) having about 60 pores per inch. The PAC is attached to the PUF by the two-step method or the slurry method.

COATING PROTOCOLS

The methods used for coating the foam to fabricate a PAC-containing composite are as follows:

A. PROTOCOL FOR "TWO STEP" COATING OF GENERAL FOAM WITH SYNTHEMUL AND PAC, (LAYERED COMPOSITE)

1) A 3"×1½"×½" slab of the foam was squeezed several times in a 50:50 mixture of commercial adhesive and water to remove all air from the foam. 2) The slab was then passed through a pasta press (roller) on #5 thickness setting which is 1.02 mm wide, then 3) immediately placed into a jar containing 11.25 g of PAC and shaken for one hour at high speed on a wrist action shaker. 4) The slab was then allowed to air dry for 2 days. 5) After drying the slab was cut into the 1"×1"×1" pieces, then 6) washed with D.I. water to remove any particles of PAC or small pieces of PUF. 7) The pieces were dried overnight.

B. PROTOCOL FOR SLURRY COATING OF GENERAL FOAM WITH SURFACTANT, PAC AND SYNTHEMUL (MATRIX COMPOSITE)

A slurry was made as follows. 1) 7.1 ml of Tween 80 was added to 102.1 ml of water and the mixture stirred until dissolved. 2) 22.7 g of PAC was added while stirring and allowed stir for 5 minutes. 3) 145 ml of Synthemul or other latex adhesive was added rapidly and the suspension stirred rapidly for another 5 minutes. The foam is then coated onto the foam using steps A1, A2, A4–A7.

One of the model polymers used was styrene butadiene copolymer. It was obtained from Aldrich Chemical. It was to be used to bind PAC to PUF to produce a phenol binding composite. When the container was opened a strong smell of styrene was noticed. Since we have demonstrated that aromatics such as toluene and xylenes are strong inhibitors of phenol binding to PAC, it was necessary that the styrene butadiene copolymer had to be freed of low molecular weight monomers and oligomers in order to make the phenol binding studies unambiguous. This was accomplished by dissolution and reprecipitation as described below.

A 10% w/v solution of the styrene-butadiene was made by dissolving 25 g of the polymer in 250 ml of tetrahydrofuran (THF) with the use of a 500 ml beaker and magnetic stirrer. The beaker was sealed with aluminum foil to retard evaporation of the THF. The styrene-butadiene was precipitated from the THF solution by addition to a non-solvent, methanol. To this end the styrene-butadiene copolymer solution was placed, in portions, in a 125 ml separatory funnel. It was added in a dropwise fashion to 2.5 liters of slowly stirred (75 RPM) methanol. Individual and aggregated beads of precipitated polymer resulted. Rapid stirring resulted in a large "golf ball" like conglomerate of precipitated polymer. The aggregates were cut up into 2–4 mm pieces and stirred in about 500 ml fresh methanol overnight. They were combined with the beads and stirred further with about 500 ml fresh methanol for 3–5 hrs. The collected precipitate was dried in a stream of nitrogen whereupon the precipitate turned from white to off white to pale yellow. The yield of styrene-buadiene copolymer was 97.7%.

In a similar fashion, polymethyl acrylate, possessing a $T_g$ of 9° C., obtained as a toluene solution from Aldrich Chemical, was freed from aromatic solvents through fractional precipitation (6269-10). One hundered ml of the toluene solution, possessing an unknown concentration of polymer, was added dropwise to 1 L of slowly stirred methanol. An oily substance, presumably the polymer, was precipitated. The solution was allowed to sit for 3–4 days but no crystalization or solidification of the oil occured. Therefore, the top layer of fluid, containing methanol, toluene and non-precipitated materials, was decanted and replaced with 1 L fresh methanol. The mixture was stirred for 6 hrs and then allowed to settle overnight. The oil was transferred to a tared 250 ml beaker with the aid of THF. Solvent was evaporated by placing in the hood overnight. The weight of the partially dried oily polymer was 26.3 g. The viscous oil was dissolved in 50 ml THF. A sample of the solution was found to be 36.1% solids by placing a weighed amount of material onto a tared glass fiber pad, completely drying the sample in air and in vacuo and reweighing.

EXAMPLE 11

The following example was conducted to observe more closely the effect of the amount of bound adhesive on the amount of bound PAC, the relation of the alpha value on the amunt of bound PAC as well as the total amount of materials consumed in preparing a support by the two-step procedure.

To quantitate the amount of each material used, all solid materials, both before and after the experiment, were dried under the same conditions, at 30° C. in a vacuum oven for 24 or more hours (constant weight). In this way all solid components used in the preparation, as well as the resultant composite, were dried to the same extent, permitting accurate materials balance measurements. Since we were testing the dependencies of amounts of materials consumed as well as activities of the resulting composite on the amount of adhesive coated onto the substratum we employed the roller system for coating. The first column in Table 2 contains the settings used for the rollers. The thicknesses that these settings correspond to are depicted in Table 1. Into eight tared jars was added 7.50 g of PAC. Into a $9^{th}$ tared container (the monitor beaker) was placed 7.5038 g. Essentially constant weight was attained in the monitor beaker at 23 hrs drying time (final weight, 7.014 g, with 0.003 g weight change in the last 1.5 hr). The weight loss is therefore 6.53%. The synthemul adhesive was diluted with an equal amount of water prior to the foam coating. General foam was cut into seven 1"×1"×3" slabs (the "large" slabs; see Table 2 for assay results and columns 6–14 in Table 3 for gravimetric data pertaining to these composites) and seven 1"×1"×1" pieces (the "small" cubes; see columns 2–5 for gravimetric data pertaining to these composites) plus a small monitor cube of foam. The pieces were dried overnight and weighed. When a piece of monitor foam was dried for 3 days in the vacuum oven it showed a 0.47% weight loss. The weights of the small PUF cubes are in column 2 Table 3. The large pieces are carried through the full coating and curing procedure and used for determining the total weight of the composite. The small pieces were used solely to determine the dry weight and % solids of the adhesive applied to the foam. The large number of pieces used for the % solids calculation ensured accurate results. The measurement of the dry solids content of the adhesive was performed on the foam and in a vacuum drying oven. This was done in order to keep the drying conditions as close to the other processing conditions as possible. For the coating procedure, the PUF was immersed in adhesive and squeezed a number of times to remove entrapped air. Then, various amounts of adhesive were expressed from the foam through the selection of various settings for the pair of rollers (i.e., set at different distances from each other). The width of the rollers and the corresponding settings are described in Table 1. The cubes and slabs of wet adhesive-coated foam were immediately weighed. These values are in columns 3 and 7, respectively, Table 3. The amount of wet adhesive bound to the cubes and slabs, determined by subtracting the starting weight of the PUF from the net weight of the wet adhesive-coated foam, is in columns 4 and 8, respectively, Table 3. In the next step, the wet adhesive-coated cubes were first air dried for one day and then dried in the vacuum oven for one day. They were used for adhesive dry weight calculations as described above. The dry weights of adhesive on the 1" cubes is depicted in column 5, Table 3. The calculated dry weight of adhesive on the slabs is given in column 10. PAC was bound to the wet, adhesive-coated slabs of PUF by immediately exposing them, two per jar, to excess PAC (7.5 g) and then agitating the mixture for 90 min. The slabs were then removed from the jars and air dried. After allowing the composite to cure completely (two days), excess PAC was first shaken off and then washed off (5×with 400 ml water, then shaken 1 hr with 400 ml water and then rinsed again with 400 ml water) and finally air dried for 3 days. The washed and air dried composite was then vacuum dried for one day (constant weight). This weight is recorded in column 11 of Table 3. Note that we did not add any cure time between addition of adhesive and addition of PAC since we have consistently found that experiments with the shortest time between coating with the adhesive and addition of the PAC yield the highest alpha value activity for phenol binding. (This lack of cure time is born out with our slurry approach. PAC slurried with the synthemul adhesive remains highly active). By subtracting the initial dry weight of PUF and the calculated dry weight of adhesive from the net dry weight of the composite we were able to calculate the weight of dry PAC on each individual piece of composite.

We then cut off, weighed and assayed a 0.5"×1"×2" portion of the 1"×1"×3" composite for its ability to bind phenol as described in the previous report. The initial phenol concentration was 95.0 ppm. The phenol concentration in the assay solution after one day equilibration is in column 2 and the difference between these two values (delta phenol conc.) is in column 3 (see Table 2).

TABLE 1

| SAMPLE | SETTING |
|---|---|
| 1 | 2.29 mm |
| 2 | 2.11 mm |
| 3 | 1.65 mm |
| 4 | 1.17 mm |
| 5 | 1.02 mm |
| 6 | 0.38 mm |
| 7 | 0.18 mm |

TABLE 2

5600–158: ASSAY OF MATERIALS USED IN QUANTITATION OF THE AMOUNT OF ADHESIVE AND PAC BOUND TO GENERAL FOAM USING 50% SYNTHEMUL AND VARIOUS PRESS SETTINGS, EMPLOYING THE TWO-STEP APPLICATION METHOD. LJD/DRW, 5600P158

| SETTING | FINAL PHENOL CONC. PPM | DELTA PHENOL CONC. PPM | SUPPRT WEIGHT GM 1" CUBE | SUPPRT WT GM OF BIG CMPSIT | DRY G PAC ON BIG CMPSIT | DRY G PAC USED IN PHENOL BINDING | ALPHA VALUE CMPOS | ALPHA VALUE PAC |
|---|---|---|---|---|---|---|---|---|
| 1 | 0.430 | 94.530 | 1.4378 | 3.9547 | 2.865 | 1.0416 | 15290 | 21105 |
| 2 | 0.300 | 94.660 | 1.7103 | 4.8187 | 3.671 | 1.3594 | 18449 | 23212 |
| 3 | 0.450 | 94.510 | 1.3108 | 3.7584 | 2.949 | 1.0291 | 16022 | 20409 |
| 4 | 0.750 | 94.210 | 1.1175 | 3.2932 | 2.479 | 0.8412 | 11241 | 14932 |
| 5 | 0.580 | 94.380 | 1.1372 | 3.1649 | 2.540 | 0.9127 | 14309 | 17830 |
| 6 | 0.790 | 94.170 | 0.9232 | 2.8498 | 2.242 | 0.7263 | 12912 | 16412 |
| 7 | 1.503 | 93.457 | 0.7251 | 2.4053 | 1.861 | 0.5610 | 8575 | 11084 |

ASSAY VOLUME = 100.0 ML; INITIAL PHENOL CONC. = 95.0 PPM

TABLE 3

QUANTITATION OF THE AMOUNT OF ADHESIVE AND PAC BOUND TO GENERAL FOAM USING 50% SYNTHEMUL AND VARIOUS PRESS SETTINGS EMPLOYING THE TWO-STEP APPLICATION METHOD. LJD/DRW 5600R158

| | "SMALL" CUBE, 1" × 1" × 1" | | | | "LARGE SLAB", 1" × 1" × 3" | | | | | | | | |
|---|---|---|---|---|---|---|---|---|---|---|---|---|---|
| SETTING | G DRY 1×1×1" PUF | G WET WT PUF + ADHSV | G NET WET WT ADHSV BOUND | G DRY WT PUF + ADHSV | G DRY 1×1×3" PUF | G WET WT PUF + ADHSV | G NET WET WT ADHSV ON PUF | G WET ADH/G PUF | DRY G ADH/G PUF | DRY G COMPLT CMPST 1×1×3" | DRY G PAC | DRY G PAC/G PUF | ALPHA VALUE CMPST |
| 7 | 0.4465 | 0.8103 | 0.3638 | 0.544 | 1.2378 | 1.951 | 0.7132 | 0.576 | 0.159 | 2.4053 | 0.970 | 0.784 | 8575 |
| 6 | 0.4619 | 0.9847 | 0.5228 | 0.608 | 1.3485 | 2.432 | 1.0835 | 0.803 | 0.222 | 2.8498 | 1.201 | 0.891 | 12912 |
| 5 | 0.4492 | 1.0815 | 0.6323 | 0.6253 | 1.2797 | 3.2768 | 1.9971 | 1.561 | 0.432 | 3.1649 | 1.332 | 1.041 | 14309 |
| 4 | 0.4545 | 1.7435 | 1.2890 | 0.8146 | 1.2435 | 3.5557 | 2.3122 | 1.859 | 0.515 | 3.2932 | 1.410 | 1.134 | 11240 |
| 3 | 0.4199 | 1.8215 | 1.4016 | 0.8075 | 1.2469 | 4.6185 | 3.3716 | 2.704 | 0.748 | 3.7564 | 1.576 | 1.264 | 16022 |
| 1 | 0.4279 | 2.8013 | 2.3734 | 1.0897 | 1.2622 | 4.6418 | 3.3796 | 2.678 | 0.741 | 3.9547 | 1.757 | 1.392 | 15289 |
| 2 | 0.4171 | 2.3343 | 1.9172 | 0.9477 | 1.3772 | 5.6331 | 4.2559 | 3.090 | 0.855 | 4.6187 | 2.064 | 1.498 | 18449 |

G DRY PAC ADDED TO JAR FOR BINDING TO ADHSV-COATED PUF: AVE = 7.05 +/− 0.02
X DRY SOLIDS IN ADHSV SOLUTION APPLIED TO PUF: AVE = 27.68 +/− 0.41 some excess adhesive tends to envelope some of the PAC and thereby become available to bind additional PAC at its surface. However, this variation of amount of PAC bound vs. the amount of adhesive bound to the foam follows a rather straight line, consistent with a Langmuir-type saturation binding. This indicates that there is probably a fairly even and complete "mono-granular" coverage of the foam even with the smaller quantities of adhesive. That is, once the surface of the foam is covered with PAC little additional PAC binds. The alpha value varies with a greater proportion vs. bound PAC, approximately doubling with only a 36%

SUMMARY OF RESULTS FOR EXAMPLE 11

Varying the number of (wet) grams of synthemul/gram of PUF from about 0.6 to 3.1 only changed the number of grams PAC bound per gram of PUF from about 0.8 to 1.5. This indicates that this is probably a fairly even and complete coverage of the foam even with the smaller quantities of adhesive. Increasing the amount of adhesive only has a modest effect on adding more bound PAC possibly because increase in PAC. However, the non-linear nature of the alpha value is undoubtedly a major contributor to this phenomenon.

EXAMPLE 12

This is a comparison of alpha values using a slurry method for 4 commercial adhesives.

TABLE 4

BINDING OF PAC TO GENERAL FOAM USING AIRFLEX, ELVACE, TYLAK, AND POLYSAT ADHESIVE:

ALPHA VALUES FOR BINDING OF PHENOL BY COMPOSITE.

| SAMPLE | INITIAL PHENOL CONC. PPM | FINAL PHENOL CONC. PPM | SUPPORT WEIGHT GM | INIT. PHENOL /GM SUPPRT | VOLUME OF PHENOL (ML) | ALPHA VALUE |
|---|---|---|---|---|---|---|
| 1 AIRFLEX | 119.4 | 1.24 | 1.5098 | 79.1 | 100.0 | 6322 |
| 2 ELVACE | 119.4 | 2.31 | 1.1024 | 108.3 | 100.0 | 4590 |
| 3 TYLAK | 119.4 | 3.70 | 1.2585 | 94.9 | 100.0 | 2487 |
| 4 POLYSAT | 87.3 | 51.10 | 2.6787 | 32.6 | 100.0 | 26.4 |

For samples 1–4, % PAC (w/v) = 13.3 and % of commercial adhesive in water is 40%.

EXAMPLE 13

Using the slurry procedure, the effect of varying the amount of PAC and varying the concentration of binder in the slurry were observed.

TABLE 5

BINDING OF VARIOUS AMT'S OF PAC TO GENERAL FOAM USING TWO DILUTIONS OF ELVACE ADHESIVE: ALPHA VALUES FOR BINDING OF PHENOL BY COMPOSITE.

| SAMPLE % PAC / % ADH | INIT PHENOL CONC. PPM | FINAL PHENOL CONC. PPM | SUPPRT WEIGHT GM AFTER | INIT PHENOL PER GM SUPPORT | ALPHA VALUE |
|---|---|---|---|---|---|
| 1A 22.35 / 50.00 | 93.0 | 1.22 | 1.4949 | 62.2 | 5034 |
| 1B 22.35 / 50.00 | 93.0 | 0.98 | 1.4832 | 62.7 | 6366 |
| 2A 14.90 / 50.00 | 93.0 | 2.58 | 1.2425 | 74.9 | 2822 |
| 2B 14.90 / 50.00 | 93.0 | 4.17 | 1.0926 | 85.1 | 1950 |
| 3A 11.18 / 50.00 | 93.0 | 5.95 | 1.1176 | 83.2 | 1310 |
| 3B 11.18 / 50.00 | 93.0 | 8.55 | 0.9483 | 98.1 | 1042 |
| 4A 13.34 / 40.00 | 93.0 | 3.97 | 0.9423 | 98.7 | 2381 |
| 4B 13.34 / 40.00 | 93.0 | 3.28 | 0.9955 | 93.5 | 2749 |
| 5A 22.35 / 40.00 | 93.0 | 0.65 | 1.3345 | 69.7 | 10650 |
| 5B 22.35 / 40.00 | 93.0 | 0.52 | 1.5926 | 58.4 | 11171 |

ALL COATINGS SMOOTH AND EVEN. VOLUME ML = 100.0; 80 ML DIL ELVACE USED FOR EACH PREP.
A and B are repeated experiments. The above results show that the activity of the adsorbent support can be optimized by adjusting the concentration of binder.
As shown by samples 1A and 5A, a reduction of binder concentration from 50 to 40% changes the alpha value from 5024 to 10,650.

EXAMPLE 14

In this experiment 12.0 g of polystyrene (styrofoam cups) were dissolved in 48 g ethyl acetate. To this viscous solution was added 8 g PAC to yield a slurry. No clumping was evident. A one inch cube of 12000 series General foam was added and squeezed about times to remove excess air. Excess fluid was removed by squeezing and pressing the cube against the side of the beaker. No roller as used. In the control experiment no PAC was added to the polystyrene solution. The cubes were then assayed for phenol binding.

Although some phenol is removed from solution by the composite (75% of the phenol removed from solution yielding an alpha value of 95 vs. and alpha of 38 for the control, see Table XIV), it is obviously not nearly as good at phenol removal as the various carboxylated polymers.

TABLE V

| SAMPLE | INIT PHENOL CONC. PPM | FINAL PHENOL CONC. PPM | SUPPORT WEIGHT GM AFTER | ALPHA VALUE |
|---|---|---|---|---|
| 1. POLYSTYRENE with PAC | 109.3 | 33.15 | 2.4125 | 95.2 |
| 2. POLYSTYRENE without PAC | 115.6 | 74.84 | 1.4178 | 38.4 |

ASSAY VOLUME = 100.0 ML

EXAMPLE 15

Two additional polystyrenes (MW=45) and (MW=280 K) were tested as binders using the procedure described in the above example. The initial phenol in each assay was approximately 100 ppm in 100 ml of water. The results are shown below:

| Polymer Binder | Alpha Value |
|---|---|
| Polystyrene (MW = 45 K) | |
| w/PAC | 178 |
| control (no PAC) | 35 |
| Polystyrene (MW = 280 K) | |
| w/Pac | 109 |
| control (no PAC) | 33 |

EXAMPLE

Polymethylmethacrylate was tested as a binder using the procedure as outlined for the polystyrene experiments above, except that PMMA (12 g) is dissolved in 48 g of THF solvent. A separate control solution was prepared.

| Polymer | Alpha Value |
|---|---|
| Polymethylmethacrylate w/PAC | 1950 |
| control (no PAC) | 45 |

Comparison of Binders Based on Glass Transition Temperatures ($T_g$)

The following table is a compilation of Tg values for supports prepared using the binders as noted. In each case the support was formed by the slurry procedure under fairly similiar conditions. The table reflects the % PAC (in grams) and % binder (grams of solid) based on a wt/vol basis wherein, the remaining wt% is the grams (ml) of water. Athough the experiments were not run under identical conditions, the results should be relatively comparable.

| POLYMER | $T_g$ °C. | ALPHA | % PAC/% POL |
|---|---|---|---|
| Synthemul | −42 | 4688 | 7/20 (clumps) |
| Elvace | −25 | 4590 | 13.3/20 |
| Tylak | −11 | 2487 | 13.3/20 |
| Airflex (vinyl acetate) | −5 | 6322 | 13.3/20 |
| Polystyrenebutadiene | −2 | 3032 | 12.9/9.7 |
| Control | | 39 | |
| Polymethylacrylate | 9 | 1950 | 11.8/17.7 |
| Control | | 45 | |
| Polystyrene (food cups) | >Rm Temp* | 95 | 10/20 |
| Control | | 38 | |
| Polystyrene (MW = 45 K) | 60–93+ | 178 | 11.8/17.7 |
| Control | | 35 | |
| Polystyrene (MW = 280 K) | 100 | 109 | 11.8/17.7 |
| Control | | 33 | |

*actual $T_g$ not measured, this is an estimate.
+60–93° C. is the softening temperature.

For each control, no PAC is employed.

EXAMPLE 16

Since polystyrene is an aromatic hydrophobic polymer with a relatively high $T_g$, for which an alpha value of 95 was observed, another aromatic hydrophobic polymer with a lower $T_G$, polystyrene butadiene copolymer, was tested as a binder to see if the $T_g$ value was an important variable in obtaining a desired alpha value. Thus, 12 g of purified (reprecipitated) styrene-butadiene copolymer was dissolved in 96 g THF. Into one half of this solution was added 8.0 g of PAC yielding a unclumped suspension. The second half of the solution was employed to coat a control cube with styrene-butadiene copolymer only. The cubes of PUF were treated as described in the above example.

| | INIT PHENOL CONC. PPM | FINAL PHENOL CONC. PPM | SUPPORT WEIGHT GM AFTER | ALPHA VALUE |
|---|---|---|---|---|
| SAMPLE | | | | |
| 1 STYR-BUTD PUF W/PAC | 106.8 | 1.84 | 1.8814 | 3032.0 |
| 2 STYR BUTD PUR W/O PAC | 106.8 | 71.14 | 1.2859 | 39.0 |

BINDING OF PAC TO GENERAL FOAM USING STYRENE-BUTADIENE COPOLYMER IN THF: ALPHA VALUES FOR BINDING OF PHENOL BY COMPOSITE.

ASSAY VOLUME = 100.0 ML
A substantial amount of phenol was bound by the resulting composite (alpha value of 3032 vs. 39 for the control).

Comparison of Carbon "Coated" Foams Using Commercial Adhesive (Synthemul)

A comparison of biomass foam supports using different supports is demonstrated in the Table below. The supports were evaluated by packing glass columns, each having about 638 ml of occupied volume of fluid in which the support is placed. The column has a diameter (I.D) of 6 cm and height of 23 cm with 3 cm of the 23 cm being free at the bottom and top of the column. The column is designed for upflow of the influent. An entry sidearm is located 4 cm from the bottom of the column. The column is aerated with $O_2$ at 6 liter/hr through a glass frit (extra course) at the bottom of the column. A layer of 1" diameter tripacs (a whiffle-ball like spherical packing material) are placed above the glass frit at the bottom of the column and above the support before the outlet of the column. Each column was inoculated with about 200 ml of a phenol degrading culture. A synthetic waste stream consisting of 750 (ppm) phenol plus mineral salts as described below was pumped into the column with a hydraulic residence time (HRT) of about 24 hours. After 25.81 days, the reactors were than fed a 1500 ppm wastestream for about 24 hours at the same HRT. Reaction was continued for at least 32 days in total.

| 750 PPM PHENOL FEEDSTOCK | |
|---|---|
| Chemical | g chemical per liter |
| $KH_2PO_4$ | 0.40 |
| $(NH_4)_2 SO_4$ | 1.00 |
| $MgSO_4 \cdot 7H_2O$ | 0.20 |
| NaCl | 0.10 |
| $CaCl_2 \cdot 2H_2O$ | 0.10 |
| $NaHCO_3$ | 0.50 |
| Liquid Phenol (89.6% w/w) | 0.84 |
| Adjust pH to 7.2 with 12 N NaOH | |

The supports employed in each column are described below.

Reactor 1—the support is ½" to ⅝" cube pieces of General foam 13000 series.

Reactor 2—the support is the foam of reactor 1 with activated carbon and Synthemul adhesive applied thereto by the two-step method. A 3"×1.5"×0.5" slab of foam is immersed in a bath of Synthemul adhesive (50:50 dilution with water). Excess fluid is removed by running the foam through the rollers of a press (pasta press set a 1.02 ml). Each slab is placed in a jar with 11.25 g of PAC. The jar is shaken (3–5 shakes/sec for 1 hr). The slab was allowed to cure for 3 days (air dry). The slab is cut into ½" cubes approximately (18 cubes/slab). The cubes are washed by violently shaking the cubes in water. This removes any loosely bound PAC. The wash step is repeated 2–3 times and then air dried.

| Typical slab | Weight |
|---|---|
| 3" × 1.5" × 0.5" foam | .991g |
| Wet weight after excess adhesive removed | 3.885g |
| Weight after completed preparation (w/PAC) | 3.633g |

Reactor 3—A slurry is prepared by (1) mixing 100.21 ml of water, 7.1 ml Tween 80, 22.7 g of PAC. (2) then stir mixture for 5 min. to make a smooth slurry. (3) rapidly add 145 ml of Synthemul (50:50 dil. water). (4) stir for 5 min. (5) a 3"×1.5"×0.5" foam slab in then immersed in slurry, excess is removed as in procedure of preparation for reactor 2, and air dried for 3 days. Then cut into about ½" cubes.

Comparative Results on Relative Shock Resistance
(ppm Phenol Measured By GC/MSD)

| Reactor | On day 20 | On day 32 |
|---|---|---|
| 1 | 0.55 | 7.1 |
| 2 | 0.010 | <0.002 |
| 3 | 0.010 | <0.004 |

Figure 8:
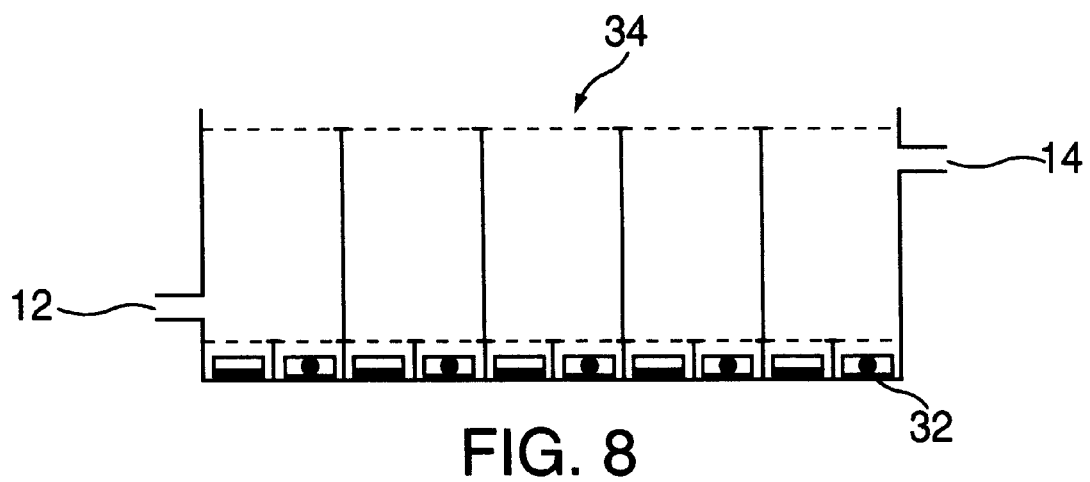
FIG. 8 is a side cross-sectional view of the reaction of FIG. 7.
Figure 9:
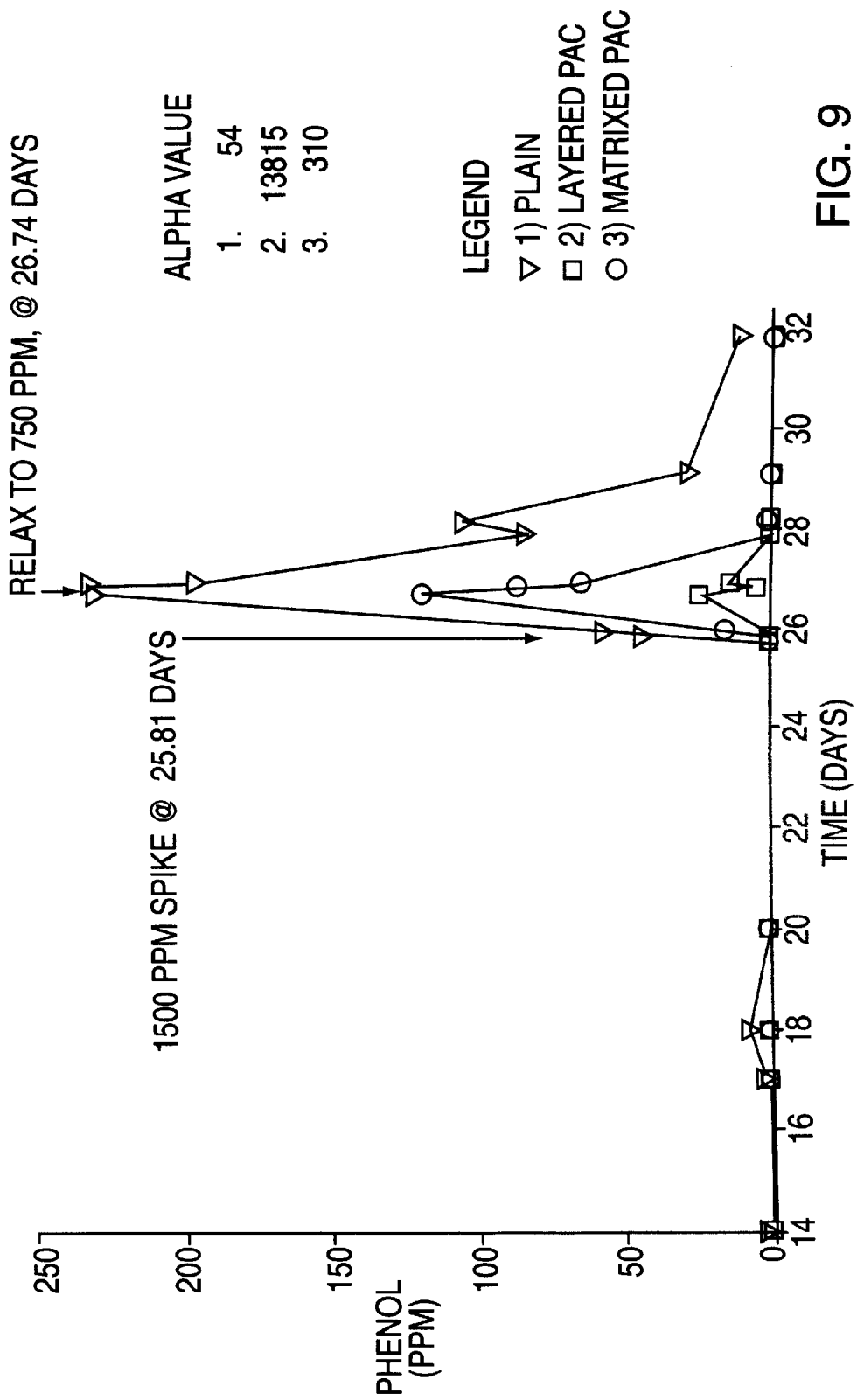
FIG. 9 is a graph of our comparative example on shock resistance.

FIG. 8 graphs the results of each reactor/support from day 1 to day 22 and the following tables shows additional measurements made using 4-AAP.

Comparative Resistance Towards Upset By PAC-Coated and Uncoated 13000 Series 13000 Series General Foam During Phenol Degradation in the ICB

| TIME ON STREAM (DAYS) | PHENOL CONCENTRATION, PPM | | |
|---|---|---|---|
| | COLUMN NO. | | |
| | INFLUENT | 1 | 2 | EFFLUENT 3 |
| 12.73 | 625 | 102 | 0.016 | 0.95 |
| 13.72 | 747 | 0.67 | 0.056 | 0.078 |
| 16.72 | 772 | 1.27 | 0.054 | 0.66 |
| 19.71 | 731 | 0.268 | 0.073 | 0.99 |
| 25.72 | 764 | 0.173 | 0.037 | 0.062 |
| 25.87 | 1584 | 43.7 | 2.390 | 0.93 |
| 25.95 | 1584 | 57.2 | 0.042 | 15.12 |
| 26.70 | 1561 | 230.0 | 24.0 | 120.0 |
| 26.84 | 694 | 231.0 | 5.0 | 87.0 |
| 26.93 | 694 | 197.0 | 14.0 | 65.0 |
| 27.72 | 694 | 84.0 | 0.235 | 0.50 |
| 27.95 | 694 | 106.0 | 0.077 | 1.153 |
| 28.99 | 712 | 29.7 | 0.042 | 0.063 |
| 31.70 | 682 | 11.7 | 0.115 | 0.194 |

The spike to 1500 ppm phenol occured at 25.81 hours. The spike ended at 26.74 hours, wherein phenol concentration was maintained at 750 ppm.

Pilot Plant Scale Up for Treating Chlorobenzene Wastestream

Further studies were conducted using a 1500 gallon upflow reactor. Approximately 1000 gal of the reactor is occupied volume of a fixed bed of support prepared by the slurry method of Reactor 3 above. A 3" cube of General Foam (13000 series) is used. The scale up follows the same ratios of adhesive, water, PAC and Tween as set up in Reactor #3 (per g of untreated foam). The slurry coated foam was squeezed through a conventional mop In squeeze cleaning bucket and air cured (2–4 days) to remove the excess slurry.

A chlorobenzene groundwater wastestream was treated. The station (A) on the following table is the concentration (ppb) of the pollutants in the groundwater as removed directly from the ground. The groundwater is then placed in a holding tank and then fed to the reactor. Station 1 is the influent feed just before the bioreactor station. Station 2 is a port at the bottom half of the reactors. Station 3 is a port at the top half of the reactor and Station 4 is the effluent Concentration levels are measured using GC/MSD. Results are summarized below.

TABLE

| STATION NUMBER | CHEMICAL CONCENTRATION (ppb) | | | | |
|---|---|---|---|---|---|
| | BENZENE | CHLORO-BENZENE | DICHLOROBENZENE ISOMER | | |
| | | | 1,3 | 1,4 | 1,2 |
| A | 940 | 3940 | 50 | 1300 | 380 |
| 1 | 360 | 2500 | — | 350 | 230 |
| 2 | <0.5 | <0.5 | <0.5 | <0.5 | 5 |
| 3 | <0.5 | 0.2 | 3 | 2 | 8 |
| 4 | <0.5 | 1 | 2 | 1 | 5 |

What we claim is:

1. A biologically active support for removal of pollutants from wastestream comprising:
   (i) a polymeric foam substrate;
   (ii) one or more particulate adsorbents which adsorb, then release said pollutants;
   (iii) a polymeric binder which binds said adsorbents to the surface of said polymeric foam substrate, wherein said binder has $T_g$ of lower than or equal to about 25° C.; and
   (iv) one or more pollutant-degrading microorganisms adhered to at least one said substrate, binder or adsorbent.

2. The support of claim 1 wherein the adsorbent is chosen from the group consisting of coal, carbon black, activated carbon, silica gel, and activated clays.

3. The support of claim 2 wherein the adsorbent is activated charcoal.

4. The support of claim 1 wherein the adsorbent is a zeolite.

5. The support of claim 1 wherein the adsorbent is a molecular sieve.

6. The support of claim 1 wherein the adsorbent is chosen from the group consisting of hydrophobic and ion exchange resins.

7. A method of making a biologically active support for use in a reactor for removal or pollutants from wastestreams comprising:
   (i) applying a layer of a curable dispersion of a polymeric binder to the surface of a polymeric foam substrate;
   (ii) then applying one or more particulate adsorbents onto the uncured polymeric binder on said polymeric foam substrate, said adsorbents which adsorb, then release said pollutants;
   (iii) allowing the binder to cure, wherein said binder binds said adsorbents to the surface of said substrate and has a $T_g$ of lower then or equal to about 25° C.; and
   (iv) exposing the binder-coated substrate of (iii) to pollutant-degrading microorganisms to adhere said microorganisms to at least one of said substrate, binder or adsorbent.

8. The support produced by the method of claim 7.

9. The method of claim 7 wherein the adsorbent is chosen from the group consisting of coal, carbon black, activated carbon, silica gel, and activated clays.

10. The method of claim 9 wherein the adsorbent is activated charcoal.

11. The method of claim 7 wherein the adsorbent is a zeolite.

12. The method of claim 7 wherein the adsorbent is a molecular sieve.

13. The method of claim 7 wherein the adsorbent is chosen from the group consisting of hydrophobic and ion exchange resins.

14. A method of making a biologically active support for use in a reactor for removal of pollutants from a wastestream comprising:
  (i) applying a coating of a curable dispersion which comprises a polymeric binder and one or more particulate adsorbents which adsorb, then release said pollutants, to a polymeric foam substrate;
  (ii) allowing the applied coating to cure, wherein said polymeric binder binds said adsorbents to the surface of said polymeric foam substrate and has a $T_g$ of lower then or equal to about 25° C.; and
  (iii) exposing the binder-coated foam substrate of (ii) to pollutant-degrading microorganisms to adhere said microorganisms to at least one of said substrate, binder or adsorbent.

15. The support produced by the method of claim 14.

16. The method of claim 14 wherein the adsorbent is chosen from the group consisting of coal, carbon black, activated carbon, silica gel, and activated clays.

17. The method of claim 16 wherein the adsorbent is activated charcoal.

18. The method of claim 14 wherein the adsorbent is a zeolite.

19. The method of claim 14 wherein the adsorbent is a molecular sieve.

20. The method of claim 14 wherein the adsorbent is chosen from the group consisting of hydrophobic and ion exchange resins.

21. A reactor for removal of pollutants from wastestreams comprising:
  (a) a container having an inlet and outlet for passage of aqueous wastestream there through;
  (b) a plurality of biologically active supports in said container, wherein each of said supports comprises:
    (i) a polymeric foam substrate;
    (ii) one or more particulate adsorbents which adsorb, then release said pollutants;
    (iii) a polymeric binder which binds said adsorbents to the surface of said polymeric foam substrate, wherein said binder has a $T_g$ of lower then or equal to about 25° C.; and
  (c) one or more pollutant-degrading microorganisms adhered to at least one of said substrate, binder or adsorbent.

22. The reactor of claim 21 wherein the adsorbent is chosen from the group consisting of coal, carbon black, activated carbon, silica gel, and activated clays.

23. The reactor of claim 22 wherein the adsorbent is activated charcoal.

24. The reactor of claim 21 wherein the adsorbent is a zeolite.

25. The reactor of claim 21 wherein the adsorbent is a molecular sieve.

26. The reactor of claim 21 wherein the adsorbent is chosen from the group consisting of hydrophobic and ion exchange resins.

* * * * *